(12) United States Patent
Marcoz et al.

(10) Patent No.: US 11,511,045 B2
(45) Date of Patent: Nov. 29, 2022

(54) DOSE CONTROL DEVICE FOR INJECTABLE-DRUG DELIVERY DEVICES

(71) Applicant: BIOCORP PRODUCTION S.A., Issoire (FR)

(72) Inventors: Alain Marcoz, Montmorin (FR); Emmanuel Jez, Clermont Ferrand (FR); Sylvain Diogo, Vergongheon (FR); Patrice Gourbet, Nonette (FR); Alexandre Pereira, Perignat-les-Sarlieve (FR); Mathieu Pollard, Pont du Château (FR); Kévin Gillet, Orcines (FR)

( * ) Notice: Subject to any disclaimer, the term of this patent is extended or adjusted under 35 U.S.C. 154(b) by 683 days.

(21) Appl. No.: 15/746,423

(22) PCT Filed: Jul. 21, 2015

(86) PCT No.: PCT/IB2015/001784
§ 371 (c)(1),
(2) Date: Jan. 22, 2018

(87) PCT Pub. No.: WO2017/013464
PCT Pub. Date: Jan. 26, 2017

(65) Prior Publication Data
US 2018/0200452 A1 Jul. 19, 2018

(51) Int. Cl.
*A61M 5/315* (2006.01)
*G01R 33/02* (2006.01)
(Continued)

(52) U.S. Cl.
CPC ......... *A61M 5/31533* (2013.01); *G01D 5/145* (2013.01); *G01R 33/0206* (2013.01);
(Continued)

(58) Field of Classification Search
CPC .......... A61M 5/31533; A61M 5/31545; A61M 5/31548; A61M 5/31568;
(Continued)

(56) References Cited

U.S. PATENT DOCUMENTS 2,885,126 A * 5/1959 Hudson .................. F02M 37/20
222/333
8,708,957 B2 4/2014 Jespersen et al.
(Continued)

FOREIGN PATENT DOCUMENTS

| CN | 103702699 B | 4/2014 |
| CN | 103957961 B | 7/2014 |

(Continued)

OTHER PUBLICATIONS

International Search Report for PCT/IB2015/001770 European Patent Office, dated Apr. 1, 2016.
(Continued)

*Primary Examiner* — James D Ponton
(74) *Attorney, Agent, or Firm* — Patshegen IP; Moshe Pinchas

(57) ABSTRACT

A dose control device adapted to be removably mounted onto an exterior peripheral surface of an injectable drug delivery device, the drug delivery device including a substantially elongate drug delivery body, at least one injectable drug held by the body, the body having a distal and proximal extremity. The dose control device includes a first component configured to fit and substantially encase at least a portion of an exterior peripheral surface of the drug delivery device, and located at a proximal extremity of the drug delivery device; a second component configured to fit and substantially encase a corresponding remaining unencased portion of the exterior peripheral surface of the drug delivery device, and also located at a proximal extremity of the drug (Continued)

delivery device. The first component and the second component removably engage with each other to form a unit having a longitudinal bore that extends along a longitudinal axis of the drug delivery device, and in which bore the drug delivery device is encased between the first component and the second component.

26 Claims, 8 Drawing Sheets

(51) Int. Cl.
*G01D 5/14* (2006.01)
*A61M 5/31* (2006.01)

(52) U.S. Cl.
CPC ............... *A61M 2005/3126* (2013.01); *A61M 2205/3317* (2013.01); *A61M 2205/3368* (2013.01); *A61M 2205/3553* (2013.01); *A61M 2205/3561* (2013.01); *A61M 2205/60* (2013.01); *A61M 2209/00* (2013.01)

(58) Field of Classification Search
CPC ....... A61M 5/3155–31555; A61M 2205/3317; A61M 2205/3368; A61M 2205/3592; A61M 2205/581; A61M 2205/582; A61M 2205/584; A61M 2205/60; A61M 2209/00; A61M 2209/01; A61M 5/31551; A61M 5/31553; A61M 5/3156; A61M 2005/3126; A61M 2205/3553; A61M 2205/3561; A61M 2205/00; G01D 5/14; G01D 5/142; G01D 5/145; G01R 33/0206
See application file for complete search history.

(56) References Cited

U.S. PATENT DOCUMENTS

| | | | | |
|---|---|---|---|---|
| 10,376,644 | B2* | 8/2019 | Krusell | .................. A61M 5/31 |
| 2002/0173702 | A1* | 11/2002 | Lebel | .................. A61M 5/168 |
| | | | | 600/300 |
| 2006/0161112 | A1 | 7/2006 | Steffen | |
| 2006/0175427 | A1 | 8/2006 | Jonientz et al. | |
| 2008/0169307 | A1 | 7/2008 | Hofstetter | |
| 2011/0295215 | A1* | 12/2011 | Nielsen | .................. G16H 20/17 |
| | | | | 604/257 |
| 2012/0022458 | A1 | 1/2012 | Oh et al. | |
| 2013/0204229 | A1* | 8/2013 | Olson | .................. A61M 5/315 |
| | | | | 604/506 |
| 2014/0197822 | A1 | 7/2014 | Ritter et al. | |
| 2014/0207080 | A1* | 7/2014 | Allerdings | ............. G16H 20/17 |
| | | | | 604/207 |
| 2015/0018770 | A1* | 1/2015 | Baran | .................. F16B 21/088 |
| | | | | 604/187 |
| 2015/0018775 | A1* | 1/2015 | Groeschke | ........ A61M 5/31551 |
| | | | | 604/207 |

FOREIGN PATENT DOCUMENTS

| | | | |
|---|---|---|---|
| DE | 102006006784 | A1 | 8/2007 |
| DE | 102008024103 | A1 | 11/2008 |
| EP | 2428238 | A1 | 3/2012 |
| EP | 1646844 | B2 | 8/2012 |
| WO | 2007107564 | A1 | 9/2007 |
| WO | 2008141619 | A1 | 11/2008 |
| WO | 2009083600 | A1 | 7/2009 |
| WO | 2012171885 | A1 | 12/2012 |
| WO | 2013004844 | A1 | 1/2013 |
| WO | 2013050535 | A2 | 4/2013 |
| WO | 2013120775 | A1 | 8/2013 |

OTHER PUBLICATIONS

International Search Report for PCT/IB2015/001784 European Patent Office, dated May 9, 2016.
Office Action—CN2015800832091; dated Apr. 20, 2020.
Office Action—CN201580082889.5; dated May 22, 2020.
Office Action—IN201827006268; dated Sep. 23, 2020.
Office Action—JP2018522884; dated Aug. 21, 2020.
Office Action—JP2018522885; dated May 17, 2019.

* cited by examiner

DOSE CONTROL DEVICE FOR INJECTABLE-DRUG DELIVERY DEVICES

The present invention relates to the field of injectable-drug delivery devices, and in particular, to dose control systems provided for such injectable-drug delivery devices.

Delivery devices for injectable drugs have been known for many years. As demands have progressed and evolved for more patient responsibility in the management of their own individual treatments and medication plans, various drug delivery devices have been developed that allowed a user to self-inject their drug. This is particularly the case, for example, with insulin, intended to treat the consequences of diabetes. However, other drugs also fall into this category, required for example, to address potentially life-threatening situations, and enabling immediate emergency injection of a required drug, such as anaphylactic shock treatments, anticoagulants, opioid receptor agonists and antagonists, and the like, to the extent that it has become a common occurrence for patients suffering from, or susceptible to, such ailments to carry these devices around with them.

One of the known problems with the existing self-injector systems was that of dosage control. In previous generations of injectable-drug delivery devices, such devices were equipped with mechanical means in order to attempt to prevent or limit excessive dose injections, or over use of the device, and the potentially serious consequences of such abuse, misuse, or simply user error. Additionally, it was felt desirable to be able to inform the user how much of the drug they had self-injected, so that there might be at least some visible cue as the injected amounts, thereby facilitating management of the treatment regime.

The main problems associated with the mechanical solutions proposed was that the necessarily over-complexified the structure of the drug deliver devices, and quite often imposed a very strict or complicated modus operandi on the user, which often could be different to that to which the user was accustomed, thereby leading to yet further manipulation errors, lost drug doses, patient non-compliance, and numerous other difficulties.

To counter these difficulties, attempts were made to address the complex nature of purely mechanical solutions involving moving mechanical parts and mechanical interactions of small and fragile components, through the use of contactless sensors and an information processing system built into the device to indicate the frequency and dose amounts of injectable drug administered, wasted, purged or otherwise expelled from the drug delivery device. This led to multiple different technical solutions, however, each one was geared to the specifics of the particular manufacturer's corresponding range of injectable-drug delivery devices.

For example, in U.S. Pat. No. 8,708,957B2, a drug delivery device for self-injection of an injectable drug is disclosed comprising a sensor which is adapted to generate pulses during injection as the delivery movements progress. The number of pulses accumulated during dose delivery correspond to the size of the dose being delivered, whereas the frequency of the detected pulses is proportional to the dose speed during injection.

In other embodiments, the sensor circuitry can include position sensors adapted to monitor specific components of the drive mechanism which move during injection. The position sensors can be either linear sensors or rotary sensors, the particular choice of sensors being selected in accordance with the specific design of the dose setting and injection mechanism. For example, a linear position sensor can be provided that monitors the movements of the piston rod during injection. Alternatively, position sensors are provided which record the movements of a component which moves in synchronism with the piston rod during injection. For example, a component being rotatably mounted in the device and which rotates during injection may be monitored by a rotary position sensor whereby the dosing speed may be calculated from the rotary movement of the rotatably mounted component during injection.

EP1646844B2 discloses an injection device for administering and injectable drug, the device comprising a non-contact measuring unit for measuring a position between elements of a dosing device, and which can be moved relative to one another, the measuring unit comprising a magneto-resistive sensor, fixed to a first element, opposite a second magnetizable element, movable relative to the first element, and embodied as a rotational element for measuring rotational position; and a magnetic device formed from a permanent magnet on the first element, and a second magnetizable element with a predetermined surface profile such that when the first and second elements are moved relative to each other, a surface of the second element changes its distance from the permanent magnet of the first element, whereby a measurable change in resistance is generated in the magneto-resistive sensor due to the change in magnetic field. This is a fairly complex system with many additional moving parts built into the barrel, or body, of the injectable-drug delivery device, leading to a greater risk of potential failure of the various components, or potentially interfering interaction between the movements of the magnet and magnetizable elements, and the respective signals generated.

EP2428238A1 discloses an apparatus apparatus for measuring a dose in an injector, comprising a number sleeve that passes through an injector body and is connected to the injector body to be spirally movable, a pattern for dose measurement being formed on an outer periphery of the number sleeve; and the injector body comprising a sensor for sensing the pattern formed on the number sleeve when the number sleeve performs a spiral movement; and a controller for measuring a dose according to a spiral movement distance of the number sleeve through the sensor. In this device, a magnet is displaced spirally along the body of the drug delivery device, which is provided with corresponding sensors located at various points along and around the longitudinal axis of the body of the drug delivery device. Once again, this solution is extremely complex, and adds further complexity to an already complex drug delivery device.

WO 02/064196 A1 discloses an injection apparatus controlled by a closed switch unit comprising integrated sensors which monitor selected parameters of the apparatus. The closed switch unit is fixed within the injection apparatus. At least two pairs of integrated Hall elements are used as the sensors. The Hall elements co-operate with a magnetized ring which alternately exhibits north and south poles. The ring is arranged within a dosing means and is moved around the longitudinal axis of the injection apparatus in accordance with a rotational movement for setting a product dosage. In order to measure the volume of a dosage setting, it is necessary to determine the rotational movement of the magnetic ring relative to the closed switch unit.

US20060175427A1 discloses an injection apparatus comprising at least one passive, non-contact sensor which can generate signals for detecting the position of a setting element, the at least one passive, non-contact sensor comprising a magnetic switch or Reed contact. According to some embodiments of the present invention, a passive component such as a magnetic switch or Reed contact may be used as the sensor, as opposed to using active components, such as optical recorders or Hall sensors. No power flows when the passive sensor is in its resting state due to the circuit being interrupted by the magnetic switch or Reed contact. The passive, non-contact sensor generates digital signals, i.e. ON and OFF, which switch on or activate a measuring circuit and switch it off again, in order to detect the position of a setting element by counting the switching-on and switching-off processes. The position of a setting element such as a rotational position of a dosing unit can be detected without energy, such as power, in order to ascertain whether a setting element has been altered or not.

WO2013050535A3 discloses a system comprising a sensor assembly adapted to measure a magnetic field, and a moveable element adapted to be moved relative to the sensor assembly between two positions by a combined axial and rotational movement, the rotational movement having a pre-determined relationship to the axial movement. A magnet is mounted to the moveable element and configured to generate a spatial magnetic field which relative to the sensor assembly varies corresponding to both the axial and rotational movement of the magnet and thus the moveable element. A processor is configured to determine on the basis of measured values for the magnetic field an axial position of the moveable element. In this system, a magnetic field producing means is located on a longitudinal drive screw that is located within the body of the injectable-drug delivery device, and the sensors are located along a longitudinal axis of said drug delivery device. It is noted that the whole of this system is located once again within the main body of the drug delivery device, in order for the magnetic field to be generated as close as possible to the longitudinal axis along which the magnet moves, and the sensors.

WO2014161954A1 discloses a drug delivery system, wherein the housing of the drug delivery device further comprises, integrated inside said housing, a first rotational member adapted to rotate relative to the housing corresponding to a set and/or expelled dose and comprising a first force transmitting surface, a second rotational member adapted to rotate relative to the housing corresponding to a set and/or expelled dose and comprising a second force transmitting surface, wherein at least portions of the first and second force transmitting surfaces are adapted to engage each other during setting and/or expelling of a dose, wherein the first rotational member comprises a magnet producing a magnetic spatial field which varies corresponding to the rotational movement of the first rotational member, and wherein the first rotational member is fully formed from a polymeric material containing magnetic particles, the polymeric material having been magnetized to provide a magnet producing the magnetic spatial field.

All of the above solutions involve a fairly complex arrangement of various sensors and/or organisation of elements within the body of the drug delivery device, which moreover generally imply having to modify said drug delivery device fairly substantially.

Accordingly, it is an object of the invention to provide a dose control device that can function with any of the currently available injectable-drug delivery devices, but which will also function with future designs of such injectable-drug delivery devices, where they rely on the general pen-shape auto-injector design, in which the drug delivery device comprises a substantially elongate drug delivery body, at least one injectable drug held by the body, the body having a distal and proximal extremity. Additionally, it is another object of the present invention to provide such a dose control device which does not require substantial modification of the injectable-drug delivery device or the way in which it functions for the user, i.e. its modus operandi, when compared to a like, off-the-shelf drug delivery device. It is yet another object of the present invention to provide a dose control device that is removably mounted on said injectable-drug delivery devices, such that the drug delivery devices can be exchanged, for example, in case of damage to the drug delivery device or malfunction in the drug delivery device, or simply because some drug delivery devices are configured to only deliver a small range of available doses of drug, and it is desirable to be able to switch to another drug delivery device that has a different range of available doses of drug. These and other objects will become apparent from the various embodiments as indicated and detailed hereinafter.

Accordingly, one embodiment of the present invention is a dose control device adapted to be removably mounted onto an exterior peripheral surface of an injectable drug delivery device, the drug delivery device comprising a substantially elongate drug delivery body, at least one injectable drug held by the body, the body having a distal and proximal extremity, wherein the dose control device comprises:
  a first component configured to fit and substantially encase at least a portion of an exterior peripheral surface of said drug delivery device, and located at a proximal extremity of said drug delivery device;
  a second component configured to fit and substantially encase a corresponding remaining unencased portion of the exterior peripheral surface of said drug delivery device, and also located at a proximal extremity of said drug delivery device;
  wherein said first component and said second component removably engage with each other to form a unit having a longitudinal bore that extends along a longitudinal axis of said drug delivery device, and in which bore the drug delivery device is encased between said first component and said second component.

According to another embodiment of the dose control device of the invention, the drug delivery device comprises a dose selector shaft, aligned substantially coaxially with the longitudinal axis of the drug delivery device, and the dose control device further comprises a substantially annular component that is mounted on said dose selector shaft and which engages therewith, and configured to impart a rotational movement about said longitudinal axis to said dose selector shaft.

According to yet another embodiment of the dose control device of the invention, the substantially annular component comprises means for producing a three-dimensional magnetic field.

In yet another embodiment of the present invention, the means for producing a three-dimensional magnetic field is an annular magnet with a first magnetic pole and a second magnetic pole of opposite polarity to the first magnetic pole, the two poles being diametrically opposed within the annular magnet.

In another embodiment according to the invention, each of the two diametrically opposed poles is substantially located in a respective half of the substantially annular component.

In still yet another embodiment of the dose control device according to the invention, wherein the three-dimensional magnetic field producing means is selected from the group consisting of ferrite, sintered ferrite, magnetic particles bound in a polymer matrix, such as composite materials consisting of a thermoplastic matrix and isotropic neodymium-iron-boron powder, composite materials made up of a thermoplastic matrix and strontium-based hard ferrite powder, composite materials made of a thermo-hardening matrix and isotropic neodymium-iron-boron powder, magnetic elastomers produced with heavily charged strontium ferrite powders mixed with synthetic rubber or PVC, flexible calendered composites formed from a synthetic elastomer charged with strontium ferrite grains, laminated composites of flexible calendered composites co-laminated with a soft iron-pole plate, neodymium-iron-boron magnets, magnetized steels made of aluminium-nickel-cobalt alloy, and alloys of samarium and cobalt.

In yet another embodiment according to the invention, said device comprises a dose control system located in said first or said second component, or distributed between said first component and said second component.

In an alternative embodiment, said control system is located within a generally annular shaped component and removably mounted around a proximal extremity of the body of the drug delivery device.

In another embodiment of the present invention, the dose control system further comprises said three-dimensional magnetic field producing means.

According to another embodiment of the present invention, the dose control device further comprises grip facilitating means for facilitating grip of the first and/or second component on the exterior peripheral surface of the drug delivery device.

In yet another embodiment of the present invention, the device further comprises an elastomeric lining located on an inner surface of said first, and/or said second component, to increase grip of said first and/or said second component on the exterior peripheral surface of the drug delivery device.

According to yet another embodiment of the device according to the invention, said first component and or said second component, either individually, or in cooperation, comprise a substantially annular portion or semi-annular portion, which engages with the outer peripheral surface of the proximal extremity of the drug delivery device.

In still yet another embodiment of the invention, said first component or said second component comprises a display window for display of a selected dose of injectable drug.

In a further embodiment of the invention, the substantially annular component further comprises grip facilitating means for facilitating grip of an inner surface of the substantially annular component on an exterior surface of the dose selector shaft.

In yet another embodiment of the invention, the dose control system comprises magnetic field detection means configured to detect changes in at least the magnetic field produced by the three-dimensional magnetic field producing means.

According to another embodiment of the device according to the invention, the dose control system further comprises at least one magnetometer, and preferably, two magnetometers.

In still yet another embodiment of the invention, the dose control system further comprises displacement detection means configured to measure a relative displacement or relative movement of the drug delivery device in a predetermined direction.

In yet another embodiment according to the present invention, the dose control system further comprises at least one accelerometer.

In a further embodiment of the device according to the present invention, the dose control system further comprises temperature detection means.

According to another embodiment of the device according to the invention, the dose control system further comprises an integrated processing unit, wherein the integrated processing unit is connected to the magnetic field detection means, and to the displacement detection means, for processing information received from both the magnetic field detection means and the displacement detection means.

In another embodiment according to the invention, the three-dimensional magnetic field producing means is configured to effect a rotating coaxial displacement around, and along, the longitudinal axis of the drug delivery system.

In a further embodiment of the invention, the magnetic field detection means and the displacement detection means are located along said longitudinal axis of the drug delivery system.

According to still yet another embodiment of the invention, the integrated processing unit is mounted on a printed circuit board located within said first component or said second component.

In a further embodiment of the invention, the magnetic field detection means is further configured to detect the earth's magnetic field (EMF).

In still yet another embodiment of the invention, the magnetic field detections means comprises at least a first and second magnetometers, wherein the first magnetometer and the second magnetometer are configured to operate in parallel, both magnetometers simultaneously detecting any changes in magnetic field, as the three-dimensional magnetic field producing means is displaced away from or towards them.

In an alternative embodiment of the invention, the magnetic field detections means comprises at least a first and second magnetometers, wherein the first magnetometer and the second magnetometer are configured to operate in series, whereby the first magnetometer detects changes in magnetic field until a predetermined value of magnetic field is detected, and then the second magnetometer is activated to detect changes in magnetic field beyond said predetermined value, as the three-dimensional magnetic field producing means is displaced away from or towards them.

In still yet another embodiment of the invention, the displacement detection means comprise at least one accelerometer configured to detect:
  the relative movement of acceleration caused by a vibration of the dose selector shaft; and/or
  a priming movement of acceleration of the dose selector shaft along the longitudinal axis of the drug delivery device; and/or
  an injection positioning of the device indicating that said device is in a position ready for an injection operation to occur; and/or
  a purge position of the device indicating that said device is in a position ready for a purge operation to occur; and/or
  a position of the drug delivery device anywhere between an injection position and a purge position.

According to a further embodiment of the invention, the dose control system further comprises communication means configured to enable communication of information from the integrated processing unit with a remote and/or local data processing system.

In still another embodiment of the invention, the dose control system further comprises a unique identifier that is communicated to the remote and/or local data processing system.

In another embodiment of the invention, the dose control system further comprises time determination means.

In a further embodiment of the invention, the dose control system further comprises autonomous power supply means.

In still yet another embodiment of the present invention, said dose control system is configured to permit an unhindered or unchanged modus operandi of said drug delivery system when compared to an injectable-drug delivery device without said dose control device.

As mentioned in various embodiments of the invention, the dose control system comprises means for producing a three-dimensional magnetic field. The magnetic field producing means produces a magnetic field that extends over three mutually perpendicular axes, x, y and z. As will be seen with regard to the detailed description of the invention, this three-dimensional magnetic field is used to calculate an angular rotational position in the dose control system of the magnetic field producing means in relation to the longitudinal axis of the body of the injectable-drug delivery device, and when that angular rotational position is known, calculate the corresponding dose.

Various means for producing a magnetic field can be used in the present invention, for example, classical magnets, electromagnets, mixed material material magnets, and the like all of which are generally known in the art. Such magnets are typically made from magnetizable materials, having magnetic or paramagnetic properties, whether naturally or when an electric or other energizing flow traverses or affects said material to produce or induce a magnetic field in said material. Suitable materials can be appropriately selected from:

ferrite magnets, especially sintered ferrite magnets, for example, comprising a crystalline compound of iron, oxygen and strontium;

composite materials consisting of a thermoplastic matrix and isotropic neodymium-iron-boron powder;

composite materials made up of a thermoplastic matrix and strontium-based hard ferrite powder, whereby the resulting magnets can contain isotropic, i.e. non-oriented, or anisotropic, i.e. oriented ferrite particles;

composite materials made of a thermo-hardening matrix and isotropic neodymium-iron-boron powder;

magnetic elastomers produced with, for example, heavily charged strontium ferrite powders mixed with synthetic rubber or PVC, and subsequently either extruded into the desired shape or calendering into fine sheets;

flexible calendered composites, generally having the appearance of a brown sheet, and more or less flexible depending on its thickness and its composition. These composites are never elastic like rubber, and tend to have a Shore Hardness in the range of 60 to 65 Shore D ANSI. Such composites are generally formed from a synthetic elastomer charged with strontium ferrite grains. The resulting magnets can be anisotropic or isotropic, the sheet varieties generally having a magnetic particle alignment due to calendaring;

laminated composites, generally comprising a flexible composite as above, culminated with a soft iron-pole plate;

neodymium-iron-boron magnets;

steels made of aluminium-nickel-cobalt alloy and magnetized;

alloys of samarium and cobalt.

Of the above list of magnetic field producing means, those comprising a polymer matrix, e.g. a thermopolymer matrix, and magnetic or magnetizable particles embedded therein, have been found to give particularly good results, as they can be injection moulded into various desired configurations, and provide a magnetic field of suitable strength, which for the present invention is a magnet producing a magnetic field of between approximately 0.5 gauss and about 32 gauss. These products are generally also known as plastomagnets, a range of which are available from Arelec (France).

As will be seen in the detailed description given hereafter, the three dimensional magnetic field producing means are substantially annular shaped. By "substantially annular shaped", it is to be understood that the magnetic field producing means defines a general ring shape, which could be circular, elliptoid, or even any suitable polygonal shape. In some instances, the magnetic field producing means could be made up of one or more separate or discontinuous segments of magnetic field producing material, for example, arcuate, quarter-spherical, or hemi-speherical, each with at least one pair of opposing magnetic poles. It is however preferred that the substantially annular ring shaped three-dimensional magnetic field producing means be made of a single block of magnetic or magnetizable material, and whilst it is possible to provide a multipolar block of magnetic field producing means, it is preferred to have only two magnetic poles, one being the opposite in polarity of the other, in the three-dimensional magnetic field producing means.

The three-dimensional magnetic field producing means of the present invention is configured to effect a rotating coaxial displacement around, and optionally along, a longitudinal axis of the drug delivery system. The rotating displacement coincides with that of a dose selector shaft, meaning that turning the magnetic field producing means around the longitudinal axis causes said shaft to rotate in the same direction, and to generate a clicking sound. Additionally, as is generally applicable to drug delivery devices equipped with such dose selector shafts, the magnetic field producing means can translate longitudinally with the dose selector shaft away, i.e. proximally, from the proximal extremity of the body of the drug delivery device, when increasing the dose to be injected. Conversely, the magnetic field producing means will rotate in the opposite direction and can translate longitudinally along the longitudinal axis of the device distally, back towards the proximal extremity of the device as the dose is reduced. In another embodiment according to the invention, the dose selector shaft is not configured to enable longitudinal translation, meaning that the dose selector shaft is simply configured to rotate about the longitudinal axis, and that this rotational movement defines the doses selected, whether clockwise or counter-clockwise. The dose control system can accordingly be adapted to such a drug delivery device also.

In addition, the magnetic field producing means is dimensioned to provide sufficient magnetic field to be detected by the magnetic field detection means, but also so as to not add extra volume to the dose control system, and thereby hinder the user or usage of the drug delivery device in normal operation when compared to a drug delivery device that has no such dose control system according to the invention.

In the dose control system according to the present invention, magnetic field detection means are present and configured to detect changes in at least the magnetic field produced by the three-dimensional magnetic field producing means. Additionally, said magnetic field detection means can also be configured to detect the earth's magnetic field (EMF), which is always present on earth, and which varies slightly from place to place. One of the reasons to include detection of the earth's magnetic field is to be able to exclude any interference caused by said field and the changes detected in the magnetic field produced by the magnetic field production means. The magnetic field detection means are used mainly to measure changes in magnetic field produced by movement of the magnetic field producing means, and as will be seen from the detailed description, to calculate an angular rotational position of the magnetic field producing means in order to determine a selected dose for administration via the injectable-drug delivery device. There are naturally other means suitable for detecting angular positions associated with rotational movements, for example, potentiometers, coded wheels and the like, however both of the latter are generally too voluminous for dose control systems such as the one according to the invention, particularly in regard to the fact that the system according to the invention is intended to be removably mounted to the injectable-drug delivery device, e.g. an autoinjector pen, and thus cumbersome and voluminous additional components are generally not preferred.

Other means of detecting magnetic fields to determine a rotational angular position are also known in the art. For example, magneto-resistors are a well known means, some of which are used in the prior art systems. Such magneto-resistors are often designated by their abbreviations, e.g. AMR, GMR, TMR sensors which designate the physical mechanisms by which these sensor components function. Giant magnetoresistance (GMR) is a quantum mechanical magnetoresistance effect observed in thin-film structures composed of alternating ferromagnetic and non-magnetic conductive layers. Anisotropic magnetoresistance, or AMR, is said to exist in materials in which a dependence of electrical resistance on the angle between the direction of electric current and direction of magnetization is observed. Tunnel magnetoresistance (TMR) is a magnetoresistive effect that occurs in a magnetic tunnel junction (MTJ), which is a component consisting of two ferromagnets separated by a thin insulator. Resistors that use these various properties are known per se. Whilst their use is possible in the present dose control system as the means for detecting the magnetic field and changes therein as produced by displacement of the magnetic field producing means and/or the earth's magnetic field, they are limited to dose control systems in which the magnetic field producing means, of corresponding equivalent dimensions and magnetic field strength, is moved away from said GMR, AMR, or TMR sensors by no more than about 25 mm. This would explain why most of the known prior art solutions have always integrated their sensors and magnetic field producing means within the body of the drug delivery device, in a grouped fashion, over a short distance, or else had to provide four or more aligned magneto-resistive sensors in order to cover the whole available distance of the piston length to cover all possible detectable and usable doses of the drug delivery device, which in many cases can have a maximum path length of up to 40 mm.

In light of the above, the dose control system of the present invention preferably uses magnetometers, for example, at least one magnetometer, and more preferably at least two magnetometers. These magnetometers differ from the GMR, AMR or TMR sensors in that they directly measure magnetic field strength, and changes therein. Magnetometers measure magnetic fields in two main ways: vector magnetometers measure the vector components of a magnetic field and total field magnetometers or scalar magnetometers measure the magnitude of the vector magnetic field. Another type of magnetometer is the absolute magnetometer, which measures the absolute magnitude or vector magnetic field, using an internal calibration or known physical constants of the magnetic sensor. Relative magnetometers measure magnitude or vector magnetic field relative to a fixed but uncalibrated baseline, and are also called variometers, used to measure variations in magnetic field. A suitable and preferred magnetometer for use in the dose control system according to the present invention is an ultra low-power high performance three axis magnetic sensor, available from ST Microelectronics, for example the LIS3MDL. Whilst it is preferred that the magnetometer be able to detect changes in magnetic field over three perpendicular axes, it is also envisaged to be able to measure changes in magnetic field over just two of the three axes of magnetic field produced by the three-dimensional magnetic field production means. A device such as the LIS3MDL can be configured to detect magnetic fields across a full scale up to $\pm 4/\pm 8/\pm 12/\pm 16$ gauss, however, it could also be useful and advantageous to use magnetometers that are capable of detecting even higher magnetic fields, e.g. 32 gauss. In the present invention, it thus is preferred that the magnetometer be configured to detect magnetic fields of from about 0.5 gauss to about 32 gauss.

As mentioned above, the dose control system of the present invention also comprises displacement detection means configured to measure a relative displacement or relative movement of the drug delivery device. Such displacement detection means could typically use sound, for example, as a way of registering movements in a dose selector shaft, as such dose selector shafts are often constructed so as to make a clicking noise via a toothed cylinder ratcheting against, for example, the inner wall or a corresponding depression or cavity of said inner wall matching the tooth, which when rotated about the longitudinal axis of the drug delivery device, drives the tooth in and out of said depression or cavity and causes an audible click. The clicking sound thereby facilitates any other visual cues that might be given to the user. Each click generally represents an angle of rotation of the shaft about the longitudinal axis, irrespective of direction of rotation, and corresponds to a selected dose. However, if the dose selector shaft is turned very quickly, or clockwise and counterwise in quick succession, or vice-versa, it becomes almost impossible to know which dose has been selected just by the audible cue of the clicks alone. Thus, the applicants have chosen to measure the movements induced by the vibrations of the dose selector shaft when it is turned and generates one or more clicks, as the vibration provides a relative movement that can be detected. These movements correspond to tiny accelerations, and can be detected and measured appropriately through the use of corresponding accelerometers, which are the preferred means for the displacement detection means of the present invention, as they can be configured to detect accelerational movements along three perpendicular axes, and the time between movements can be measured so as to compare against a predetermined standard set of accelerational movements for said drug delivery devices and which correspond to normal usage of the device at the various stages of its use for administering an injectable product. For example, when the drug delivery device is in a substantially horizontal position, or in either of the substantially vertical positions, i.e. purge or injection, the accelerometer detects a substantially constant signal of low frequency vibrations, which can be used as a base line for the device. Whenever the dose selector shaft, or an end button to prime the injector, or effect injection, is activated, or rotated, the vibrations generated thereby are captured as high frequency spikes compared to the low frequency baseline. These high frequency vibrations can be sampled and analyzed the results of which are then used to determine which operations have been undertaken by a user. Whilst there exist many different types of accelerometer on the market, the applicants have a preference for a low-g three-axis accelerometer, such as those available from ST Microelectronics, under the trade reference LIS331DLH. Additionally, such accelerometers advantageously also comprise means for determining temperature, i.e. they have a built-in temperature sensor, which can assist in determining whether the drug product included in the drug delivery device has been exposed to extremes of temperature likely to make it unsafe to use the drug product. It has been found particularly advantageous if the displacement detection means are located as close as possible to the source of vibrations emitted by the device.

As also indicated in preceding paragraphs, the magnetic field detection means are located along the longitudinal axis of the injectable-drug delivery device. In this way, it is possible to reduce the overall volume of the dose control system by positioning the various detection means along that longitudinal axis. A further advantage is that axial alignment avoids potential distortions of magnetic field, as might be found if the magnetic field detection means were located, for example, perpendicularly or at an angle to said longitudinal axis, and which would either interfere with the measurements, or else require more complex calculations to take into account any such distortion.

The interplay between the displacement detection means, the magnetic field detection means and the magnetic field production means is one of the advantageous combinations of features of the present invention.

The dose control system also advantageously comprises an integrated control unit connected to the magnetic field detection means, and to the displacement detection means, for processing information received from both the magnetic field detection means and the displacement detection means. This integrated control unit can be mounted on a printed circuit board, for example, of suitably reduced dimensions, e.g. approximately 45 mm long by 15 mm wide, and 1.5 mm deep. The integrated control unit handles all electrical communication and signaling between the different electronic components of the dose control system. It is also responsible for execution of the dose management system and calculations enabling precise positional locations of the magnetic field production means to be calculated and determined, as well as handling signals from the movement detection means, the autonomous power means, the communication means with a local or remote data processing system, e.g. on a smartphone. It can be programmed remotely, upon first use, or receive information and updates, in a similar way to other electronic devices today containing integrated control units. Such integrated control units are known per se, and often integrate a central processing unit, a real time clock, one or more memory storage systems, and optionally communications systems or subsystems, along with other desired components.

The dose control system of the present invention marks a clear break with the past solutions, by providing a dose control system, that is not only removably mounted on the body of the drug delivery device, but is also capable of accurately providing detection of changes in angular position due to subtle changes in magnetic field, and thereby calculating the corresponding selected dose, without having to place all of the components within the body of the drug delivery device. In fact, the dose control system of the present invention has enabled the applicants to provide a removably mountable system, that can be used with a variety of different drug delivery devices currently on the market, in particular, but not exclusively, the insulin autoinjector pens that are currently distributed for patient self-medication.

BRIEF DESCRIPTION OF THE FIGURES

The invention will be further described in relation to the accompanying figures, provided for illustrative and non-limiting purposes of exemplary manifestations of the embodiments of the present invention, in which.

DETAILED DESCRIPTION

Figure 1:
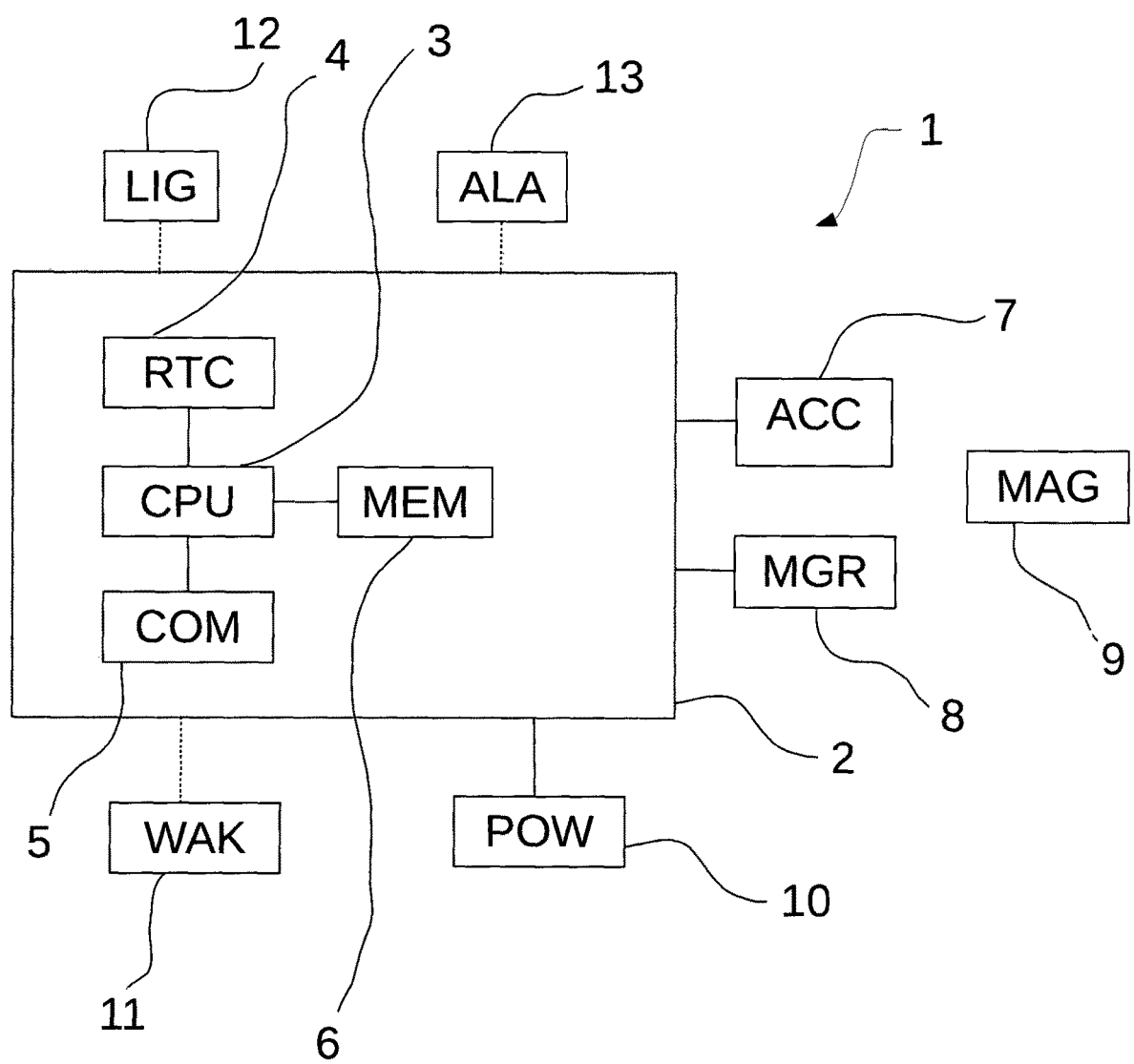
FIG. 1 is a schematic view of an example of a dose control device according to the present invention containing a dose control system.

Turning now to FIG. 1, a schematic diagram of the components of a dose control system (1) according to the present invention is displayed. Such a dose control system comprises for example, an integrated control unit (2), for example, mounted on a printed circuit board, or equivalent on which various components are mounted and in connection with each other. The integrated control unit (2) could also be comprised of circuits engraved or etched in silicon or the like, as is known per se. In fact, virtually the whole dose control system could be engraved into a single, or multiple, interconnected blocks of silicon or other similar semi-conductor material as generally known in the art if so desired. The integrated control unit (2) comprises a central processing unit (CPU, 3), which is responsible for processing and managing signals and communication between the various components of the system, and also for calculations, and execution of program code stored within the system, or operable remotely on said system. The integrated control unit (2) additionally comprises a real time clock (RTC, 4), for keeping and measuring time within the dose control system. The real time clock (RTC, 4) can also be integrated into the central processing unit (CPU, 3), for example, using frequency measurements whilst the central processing unit (CPU, 3) is powered with energy, in order to calculate time and time differences for various events within the system. The dose control system is also equipped with a communications subsystem (COM, 5), for example a low power consuming bluetooth radio device, the communications subsystem allowing for the dose control system to communicate with a local or remote data processing system (not shown), e.g. a smartphone and corresponding smartphone application, used to provide information and feedback to the user on usage of the dose control system. Additionally, the system also has some form of memory storage (MEM, 6), for storing information within the system, whether transiently or permanently, such information coming from a variety of sources, including the values or signals measured or determined from other endpoints of the system, values calculated or stored by the central processing unit (CPU, 3), values or data received from the remote or local data processing system, such as the smartphone, factory settings for calibration of the system, a unique identifier means or data identifying the device uniquely, and the like. Such memory storage systems (MEM, 6) are known per se to the skilled person.

The integrated control unit (2), and by extension, the central processing unit (CPU, 3), is also in communication with at least one accelerometer (ACC, 7) and at least one magnetometer (MGR, 8). The accelerometer (ACC, 7) is responsible for detecting and/or measuring changes in relative movement due to acceleration of the drug delivery device on which the dose control system is mounted, be it from a horizontal to vertical position as held by the user, or any position in between, with regard to a set of predetermined and pre-programmed reference positions. The accelerometer (ACC, 7) is also responsible for detecting and/or measuring changes in relative movement due to acceleration of the drug delivery device when a user sets a dosage via a dose selector shaft, which causes a vibration of the drug delivery device, i.e. a relative movement of acceleration, that is detectable by the accelerometer (ACC, 7). The strength and frequency of the relative movements of acceleration, which are communicated from the accelerometer (ACC, 7) to the central processing unit (CPU, 3) are used to determine the type of operation that the user has effected. Such relative movements of acceleration can include vibrations caused by clicks produced by the drug delivery device, e.g. in the majority of autoinjector drug delivery devices, e.g. pens, for self-injection of various drugs, e.g. insulin, ATP, and the like, these clicks provide an audible cue signal for the user to indicate various operations undertaken by the latter, but the clicks also produce vibrations within the drug delivery device that can be suitably picked up by an accelerometer.

The magnetometer (MGR, 8) is also connected to the central processing unit (CPU, 3). This component is responsible for detecting changes in magnetic field, as produced by movement of the magnet (MAG, 9) which is in a movable spaced relationship with the magnetometer (MGR, 8). The magnetometer is capable of detecting changes of magnetic field along multiple axes, for example one, two, three or more axes, although detection of changes in magnetic field along two or three axes are preferred. Usually, these axes are perpendicular to one another, so as to provide a three-dimensional magnetic field detection zone. The at least one, and preferably two, magnetometers are located so as to be able to detect corresponding changes in magnetic field as the magnet (MAG, 8) is displaced. As the drug delivery device on which the dose control system is mounted has a longitudinal axis, it is preferable to also locate the at least one magnetometer (MGR, 7) along said longitudinal axis. In a preferred embodiment, the system includes two magnetometers and these are located in axial alignment along the longitudinal axis of the drug delivery device when the dose control system is mounted on said device. This allows the dose control system to remain compact in size and dimensions, and thereby not negatively influence or interfere with normal, habitual manipulation of the drug delivery device by the user. The magnetometer is also suitably configured to detect the earth's magnetic field, and any changes therein that might occur when the user travels with the drug delivery device, as the earth's magnetic field, and changes therein can influence the measurements made by the magnetometer (MGR, 7) in regard to the magnetic field producing means of the dose control system.

The magnetic field producing means in the present exemplary device include a magnet (MAG, 9). In one particularly preferred embodiment, the magnet produces a three dimensional magnetic field along three perpendicularly positioned axes (x, y, z). As mentioned above, the magnetometer (MGR, 7) detects changes in magnetic field produced by the magnet (MAG, 9), when the latter is displaced proximally, and away from, or distally and towards, a proximal extremity of the drug delivery device. This detection of magnetic field changes occurs without any form of electrical or electronic or physical contact between the magnetometer(s) (MGR, 7) and the magnet (MAG, 9), leading to the designation of the dose control system as a contactless system. The magnet preferably has a substantially annular shape, with a hole in the middle, and can be made of any suitable magnetic or magnetizable material, details of which are given elsewhere in the present specification. The magnet (MAG, 9) can thus be mounted on a dose selector shaft of the drug delivery device, which is in longitudinal axial alignment with both the longitudinal axis of the drug delivered device and the magnetometer(s). The dose selector shaft is generally rod shaped, such that the substantially annular magnet can be removably slid onto the shaft, and produce a three-dimensional magnetic field around the proximal extremity of the drug delivery device. The magnet is removably mounted on the dose selector shaft in such a way that it can impart rotational movement to said shaft when turned by a user. Rotation can occur in both clockwise and counter-clockwise directions. The magnet has two opposing poles, each substantially constituting a half, or hemi-spherical part of the annular magnet. As the magnet rotates, the opposing poles also rotate about the longitudinal axis of the device. A first reference point of known magnetic field strength along one, two or three axes, is detected by the magnetometer(s) and this information is stored in the dose control system, for example in memory (MEM, 6), via the central processing unit (CPU, 3). Generally, this first position will correspond to a position of the magnet (MAG, 9) in which it is closest to the proximal extremity of the drug delivery device, and beyond which further rotation of the dose selector shaft in a given direction is impossible. When the user rotates the magnet (MAG, 9), in an allowed direction of rotation, and correspondingly indexed rotational movement of the dose selector shaft, the magnet and proximal extremity of the dose selector shaft move longitudinally in a proximal direction away from the proximal extremity of the body of the drug delivery device, but along the longitudinal axis of the device in general. As the magnet (MAG, 9) rotates around said longitudinal axis, and translates there along, changes in magnetic field and polarity are detected by the suitably positioned magnetometer(s) (MGR, 8). The variations in magnetic field can be resolved into mathematical components comprising vectors and moduli by the central processing unit (CPU, 3), and therefrom an angular position of rotation calculated, allowing for extremely precise determination of the angular position and distance of the magnet with respect to the magnetometer(s) MGR, 8). These positions are correlated to a dose selected or selectable by the user in a lookup table which is preferably stored within the system, or alternatively stored within a remote data processing unit, such as a smartphone, wherein the maximum and minimum distances of allowed travel and rotation of the magnet (MAG, 9) along the longitudinal axis correspond to the maximum and minimum dosages allowed by the drug delivery device. In this way, the dose control system is able to present to the user an exact representation of the dose selected by the user at any given rotational and translational movement point of the magnet (MAG, 9), without interfering or changing the usual modus operandi of the drug delivery device. In an exemplary dose control system of the invention, the magnetometer(s) are configured to be able to detect magnetic fields from between ±4 gauss to ±16 gauss, with a sensitivity, or resolution, of between about 6842 LSB/gauss at ±4 gauss to about 1711 LSB/gauss at ±16 gauss. This means that the dose control system preferably has a resolution that is able to detect changes in magnetic field corresponding to an angular rotation of the magnet and dose selector shaft of 0.9° about the longitudinal axis, but as mentioned above, the resolution and sensitivity of the various components can be configured to correspond to any drug delivery device that functions in the same way via a rotatable dose selector shaft.

Also represented in FIG. 1 are a power supply (POW, 10), which is generally a portable, autonomous power supply, for example, one or more batteries, or rechargeable power elements, capable of supplying sufficient electrical power to the entire system, even when for example, the device is not being directly manipulated. The integrated control unit (2) can additionally comprise a power management unit, that regulates power supply voltage to the system, including its various components, in order to maximise the longevity of said autonomous power supply. The power supply can also communicate with a user-activated wake-up button (WAK, 11) which allows the dose control system to be woken up by the user from a hibernating or sleeping state.

The dose control system can also further comprise a light emitting signal (LIG, 12), for example, a LED, which indicates a status of the device according to detected events or conditions and managed by the central processing unit (CPU, 3), e.g. green, red, blue and white colour emission, each colour corresponding to a certain state or condition of the dose control system.

In yet a further embodiment, the dose control system can also comprise an alarm (ALA, 13) system, in communication with the central processing unit (CPU, 3), which can be configured to emit an audible alarm, say, in the case of malfunction of the system, or in the case of a failed injection, or for any other suitable condition or event detected within the system.

Figure 2:
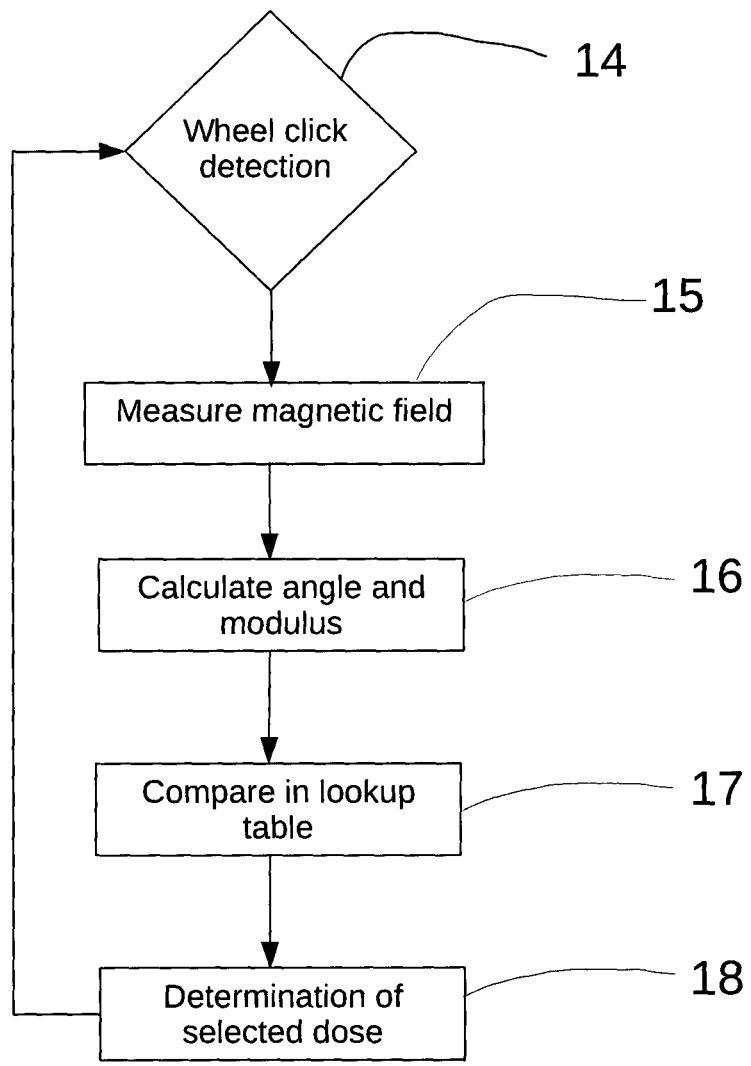
FIG. 2 is schematic flow chart of the functioning of part of the dose control system.

FIG. 2 is a schematic block diagram representation of the functioning of a dose control system according to the invention. In a first step, wheel click detection (14) of the rotating dose selector shaft is effected by the accelerometer, as the click generates vibrations which are picked up by the accelerometer (ACC, 7). The magnetic field values detected (15) by the magnetometer(s) (MGR, 8) of the magnet (MAG, 9) which rotates at the same time as the dose selector shaft are then read into the central processing unit (CPU, 3). Next, the angle and modulus of the magnetic field are calculated (16) by the central processing unit (CPU, 3). These values are correlated with, or compared to (17) a predetermined set of values that has been preprogrammed into the dose control system. Finally, a determination (18) of the selected dose is made. These steps are repeated as necessary, each time the user causes the dose selector shaft to rotate about the longitudinal axis. Once the user has decided which dose it wishes to inject itself with, a click caused by the user pressing a proximally located injector end button, which causes a vibration and corresponding movement of acceleration within the drug delivery device, is registered by the accelerometer. The frequency, or interval between each end button click is used to determine whether an injector button click is compared to a known list of pre-determined movements of acceleration to determine whether the end button click was intentional, or else the result of accidental activation of the end button or movement in the drug delivery device. If the movement of acceleration and frequency thereof do correspond to a situation in which the dose is recognized as having been deliberately selected, ready for injection, this dose is registered within the system, e.g. within memory, and communicated via the communication means to the data processing unit, for example, a smartphone application, along with the time at which said event occurred. In this way, the smartphone application is able to process that information and provide it to the user in the form of tracking or observance information.

Figure 3:
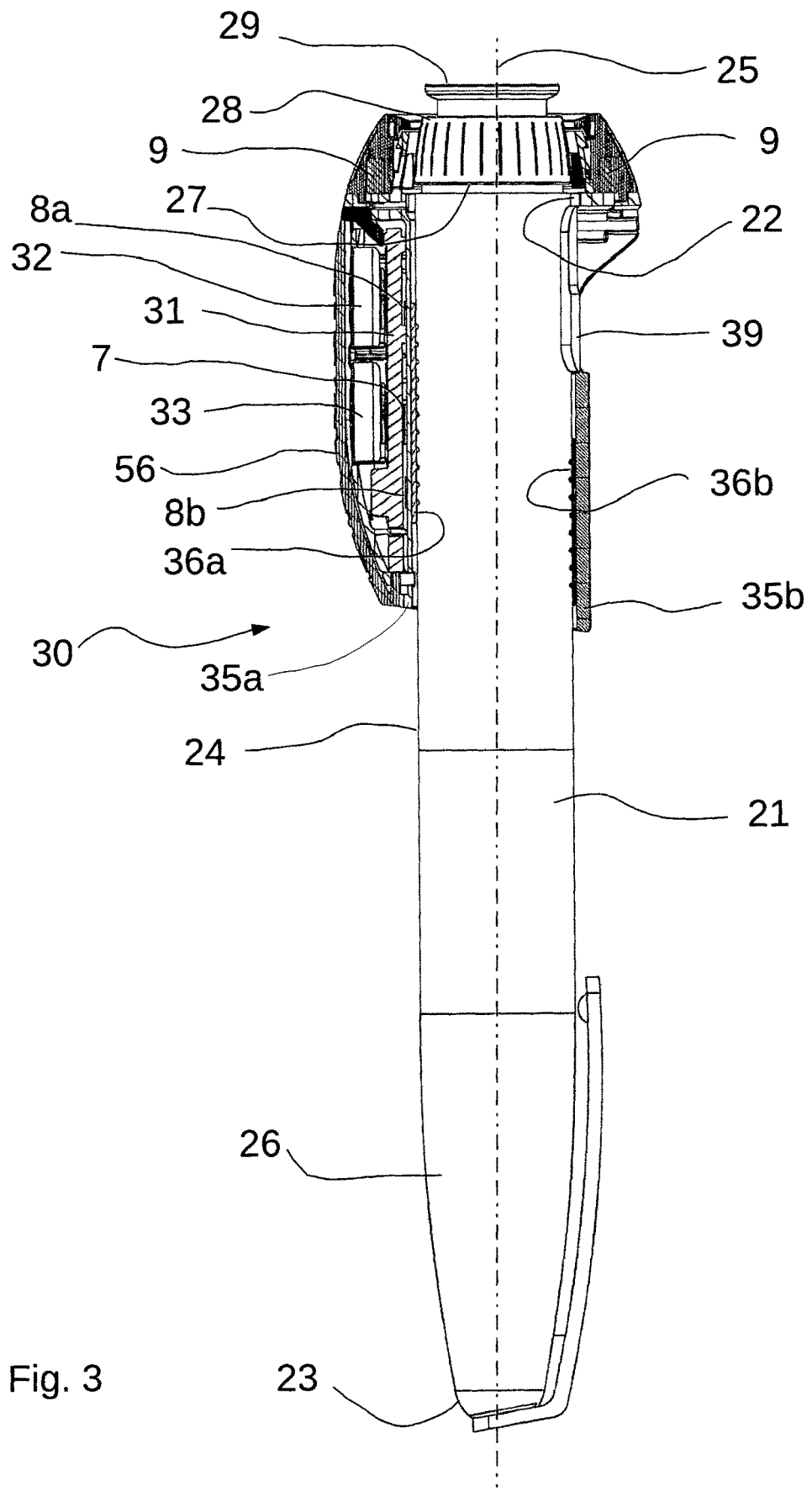
FIG. 3 is a cross-sectional schematic representation of a dose control device according to the present invention, mounted onto an injectable-drug delivery device, in this case, an insulin autoinjector pen.

FIG. 3 is a schematic cross-sectional representation of a dose control system mounted on an injectable-drug delivery device, indicated generally by the reference numeral 20. The injectable-drug delivery device (20) generally comprises a substantially elongate drug delivery body (21), having a longitudinal axis (25), at least one injectable drug held by the body (not shown), usually within a cartridge, the body (21) having a distal extremity (23) and a proximal extremity (22), and an outer peripheral surface (24). In FIG. 3, at the distal extremity (23), a cap (26), similar to a pen cap, is provided to cover the otherwise exposed needle and prevent the user from accidentally stabbing or otherwise injuring themselves. The drug delivery device further comprises, at the proximal extremity (22), a dose selector shaft (27), which is connected to a dose selector wheel (28), rotatable about the longitudinal axis, and an end button which can be pressed by the user to arm the device, thereby validating a selected dose, and effect drug injection via usual, known methods and means. This type of drug delivery device is similar to majority of drug delivery devices known to the skilled person.

Figure 4:
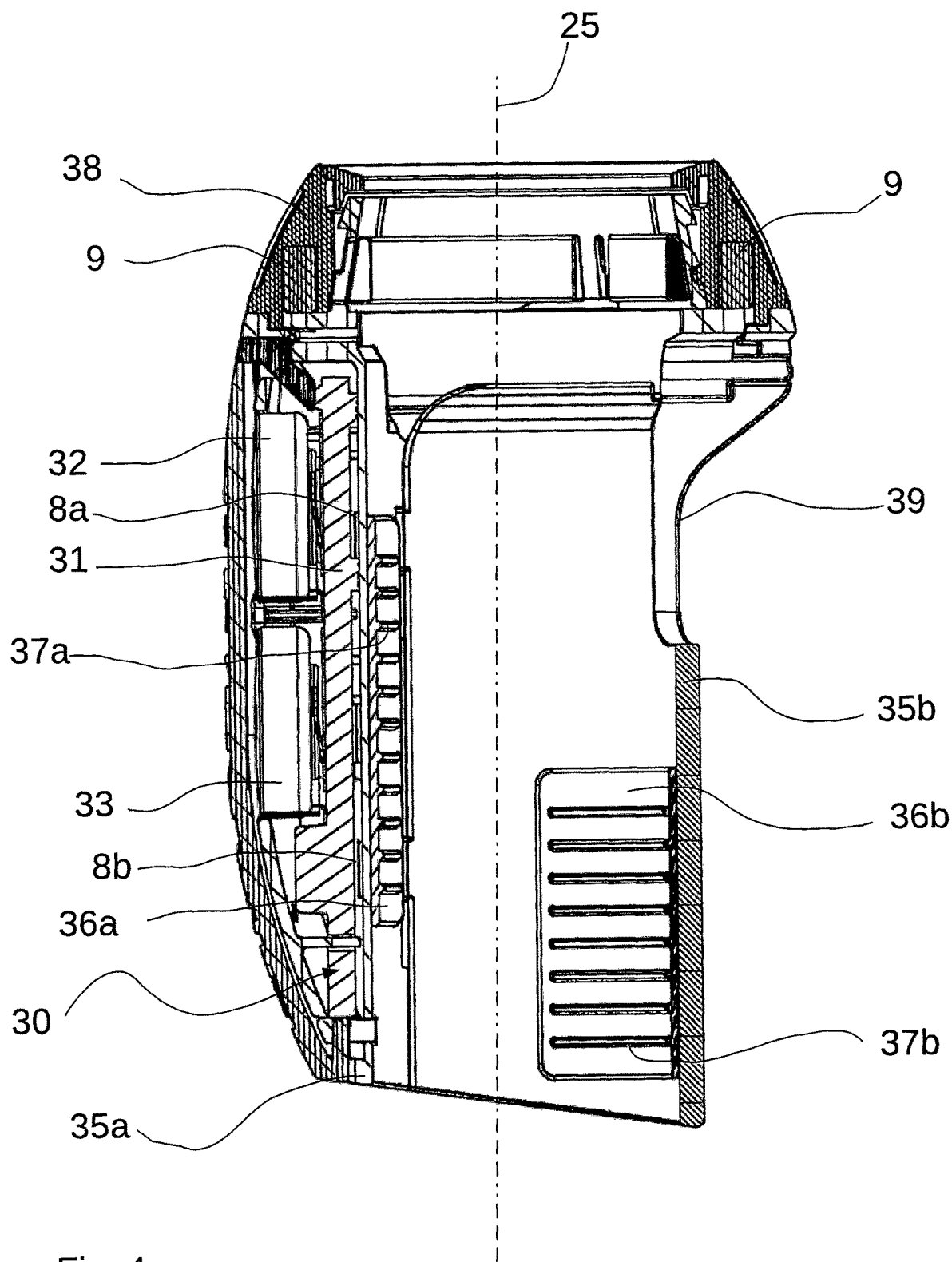
FIG. 4 is a close up schematic cross-sectional representation of a removably mountable dose control system according to the present invention, in its unmounted or "free" state.

The dose control system is indicated in FIG. 3 by the general reference numeral 30. As is apparent from FIG. 3, the dose control system (30) is located substantially at a proximal extremity of the drug delivery device (20), and is positioned on and around the outer peripheral surface (24) of the body of said device. In this particular example, the central processing unit (CPU, 3), real time clock (RTC, 4), storage memory (MEM, 6) and communications subsystem or communication means (COM, 5) are located on a printed circuit board to form the integrated control unit (2) which is encased within a polymer resin block (31). The dose control system has an autonomous power supply (POW, 10) in this example and FIGS. 3 and 4 illustrated as two batteries (32, 33), for example lithium ion batteries. The dose control system further comprises magnetic field producing means (MAG, 9), illustrated in FIG. 3 as a substantially annular shaped object which is located at the proximal extremity (22) of the device, and in a proximally spaced relationship to said extremity (22), whereby the magnet (MAG, 9) is removably mounted on the dose selector wheel (28), which in turn is connected to the dose selector shaft. As the wheel (28), shaft (27) and magnet (MAG, 9) can be caused to rotate around the longitudinal axis (25) of the drug delivery device (20), the magnet (MAG, 9) will be displaced both rotationally around said axis thereby also effecting a translational movement away from, in a proximal direction, or alternatively, towards, i.e. in a distal direction, the proximal extremity of the body (21) of the drug delivery device (20). The maximum distance of linear travel of the wheel (28), shaft (27) and magnet (MAG, 9), will generally substantially correspond to the maximum allowable dose that can be injected, and also therefore correspond to the maximum distance of travel of a piston that is usually provided to eject the drug from the cartridge in which it is held. As an example, the position nearest to the proximal extremity of the body of the drug delivery device will correspond to either no dose, or the minimum dosage. The wheel (28), shaft (27) and magnet (MAG, 9) will be blocked from rotating in a direction that would be likely to bring the latter even closer to the proximal extremity (22) of the body (21). In the opposite direction, however, i.e. in the proximal direction, the wheel (28), shaft and magnet will be able to be caused to rotate, e.g. via a user turning the magnet (MAG, 9) and wheel (28) with their fingers as many times as is allowed by the configuration of the system, and corresponding to the maximum dosage that can be injected. As the magnet, and wheel are turned, the shaft also rotates, and generates an audible clicking sound. The audible clicks correspond to a movement of acceleration transmitted through the body of the device and detected by the accelerometer (7). The rotation and longitudinal displacement of travel of the magnet (MAG, 9) causes changes in the produced magnetic field which are detected by the magnetometers (34, 35). The values detected by the magnetometers (8a, 8b) are communicated to the central processing unit (CPU, 3), and used to calculate angular position of the magnet (MAG, 9) and wheel (28) on the dose selector shaft (27) and thereby determine the dose which has been selected by the user. Priming of the injector system, via a push from the user on the end button (29), which also raises an audible click, and a corresponding linear movement of acceleration along the longitudinal axis of the device (20), is registered by the accelerometer (7). The central processing unit (CPU, 3) calculates the frequency and number of clicks produced and compares them to stored values in a lookup table to determine whether or not the device is effectively primed for injection, and if it is determined by the central processing unit that such is the case, the value of the calculated dose obtained from the changes in magnetic field is stored in memory (MEM, 6) and validated as the dose selected for injection. This value is then communicated via the communication means (COM, 5) to the smartphone application.

The magnetic field detectors can be configured to function in various ways. For example, in a serial configuration of magnetometers, i.e. when the magnetometers are aligned axially along the longitudinal axis, in a spaced apart relationship, and when the magnet (MAG, 9) is closest to the proximal extremity of the body (22) of the drug delivery device, the force of the magnetic field produced by the magnet can exceed the upper limit of the magnetometer closest to the magnet. In such a case, the magnetomer (8a) is considered to be "saturated". At this point, it is unnecessary to factor in any values detected by the second magnetometer (8b), since saturation of the first, proximal magnetometer (8a) allows for complete resolution of the angular moment and modulus when the magnet is rotated about the longitudinal axis. If the dose selector shaft is designed to also effect lateral displacement along said longitudinal axis, proximally, and away from said proximal extremity, as the magnet also moves away proximally, so does the saturation of the first proximal magnetometer (8a) drop. Once a predetermined level of magnetic field has been reached, the system is configured to activate the second, more distal magnetometer (8b), so that both magnetometers can be used to effect fine detection of smaller and smaller changes in magnetic field and angular moment, including taking into account any effects due to the earth's own magnetic field which, at the earth's surface is generally between 0.25 and 0.65 gauss. In a similar and reverse manner, when the dose selector shaft, and magnet, move distally back towards the proximal extremity of the body of the device, the second, more distal magnetometer can be automatically switched off when a predetermined higher level of magnetic field is detected. In an alternative, parallel, configuration, on the other hand, both magnetometers, whilst still aligned along the longitudinal axis of the drug deliver device, are both operational throughout all of the displacements of the magnet, and all changes in magnetic field are detected by both magnetometers.

FIG. 4 is a schematic cross-sectional representation of a housing suitable for including the dose control system of the present invention and illustrating one of several ways in which the dose control system can be mounted on an injectable-drug delivery device such as those currently known. Reference numerals remain the same between FIGS. 3 and 4 for like elements of the dose control system. The housing (35a, 35b) is designed to encase and enclose the drug delivery device (20), around and along its longitudinal axis (25) and sits removably on a peripheral outer surface (24) of said device (20). The housing is designed to snap or push fit onto the device (20) and preferably comprises at least two mating components, which engage with each other and encase the device along its body (21), along the longitudinal axis (25), at a proximal extremity (22) thereof. The housing (35a, 35b) further comprises grip facilitating means, for example a zone (36a, 36b) of compressible elastomer, locate on an inner wall of the housing, and which facilitates and increases the grip of the housing containing the dose system on the outer peripheral surface (24) of the body (21) of the drug delivery device (20) to provide a snug fit that will prevent the housing (35a, 35b) from moving relative to the body of the drug delivery device until such time as the housing is to be removed, for example, if the drug delivery device malfunctions, or the cartridge is empty or quite simply if it is desired to switch the dose control system to another drug delivery device (20). The housing is designed preferably to be snap fit, enabling it to be removed according to a predetermined set of steps, wherein each part of the housing (35a, 35b) is removed according to a sequence, without destroying or damaging the dose control system (30) contained therein, or the drug delivery device (20). The zone of compressible elastomer (36a, 36b) can further comprise compression facilitating ridges or dips (37a, 37b), i.e. added or removed elastomeric material in spaced apart arrangement along the the length and breadth of the zone (36a, 36b) so as to increase or decrease grip of the housing (35a, 35b) on the outer peripheral surface (24) of the device (20). The housing (35a, 35b) additionally provide a window (39) allowing a user to see an analog or digital representation of the selected dose, which is generally located and displayed on the outer peripheral surface (24) of the body (21) of the drug delivery device (20). The dose control system containing the magnetic field producing means (MAG, 9) is housed in a separate housing (38) that is located, and fits snugly with, the wheel (28). This magnet housing (38) is designed in a similar way to the housing (35a, 35b) of the other components of the dose control system to able to be removably snap or push fit onto the wheel (28) of the dose selector shaft (27) and can also advantageously comprise grip facilitating means, for example a zone of elastomeric material enabling the magnet housing (38) to surround and encase the wheel (28).

Figure 5:
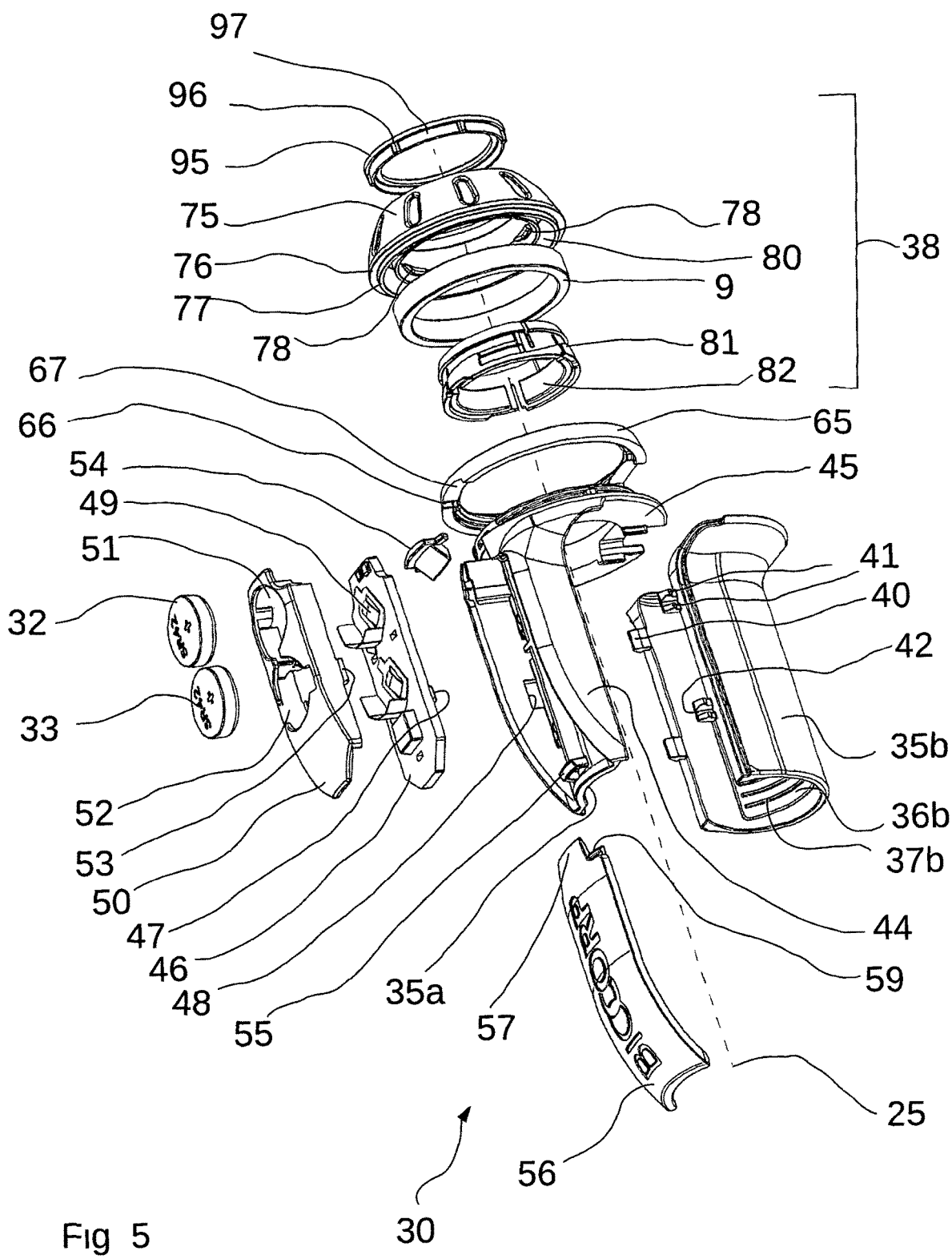
FIG. 5 is an exploded false perspective representation of a dose control device according to the present invention.

Turning now to FIG. 5, and in conjunction with FIG. 3, one can see the dose control device according to the present invention with its major elements in an exploded, false perspective view, seen slightly from above. The device in this embodiment comprises three main components:

a first component, identified as housing 35b;
a second component, identified as 35a;
and a third component, identified as 38.

The first component (35b) is configured to fit and substantially encase at least a portion of an exterior peripheral surface of a drug delivery device, and is located at a proximal extremity of said drug delivery device (cf. FIG. 3). The second component (35a) is configured to fit and substantially encase a corresponding remaining unencased portion of the exterior peripheral surface of said drug delivery device, and also located at a proximal extremity (22) of said drug delivery device (cf. FIG. 3). The first component (35b) and second component removably engage with each other to form a unit having a longitudinal bore that extends along a longitudinal axis (25) of said drug delivery device, and in which bore the drug delivery device is encased between said first component (35b) and said second component (35a). In most of the injectable-drug delivery devices on the market today, said drug delivery device also comprises a dose selector shaft (27) on which is mounted a dose selector wheel (28). As can be seen from FIG. 3 the drug delivery device comprises a dose selector shaft, aligned substantially coaxially with the longitudinal axis (25) of the drug delivery device, and the dose control device further comprises a substantially annular component (38) that is mounted on said dose selector shaft (27) and which engages therewith, and is configured to impart a rotational movement about said longitudinal axis (25) to said dose selector shaft (27). The annular component (38) comprises several elements assembled so that the annular component can be press or push-fitted onto the dose selector wheel (28) where it remains until it is removed or unmounted by the user. The various elements of the annular component (38) are configured and assembled so that they can not be disassembled by the user, however, the annular component as a whole can be unmounted from the wheel (28) and selector shaft (27). The push-fit mounting of the annular housing (38) on the wheel (28) and selector shaft (27) is such that rotating the annular component (38) will rotate the wheel (28) by exactly the same degree of rotation about axis (25) with no slip. The various elements of the annular component will be described in more detail hereinafter.

The first component (35b) is designed to envelope and encase a substantially lower part of the body of the drug delivery device, but also, as in the present figures, an upper part of said body, leaving a small surface area unencased. To this end, the first component (35b) has a substantially U-shaped cross section, and on its inner surface, i.e. the surface that comes into contact with the body of the drug delivery device, it is optionally, but preferably, equipped with grip facilitating means (36b), such as a layer of compressible elastomer. This elastomer layer (36b) is designed to that it can be compressed when assembling the first component and second component, as will be further described hereinafter, and bear onto the outer peripheral surface of the drug delivery device body (21). The elastomeric layer (36b) can have a counterpart layer (36a) on the inner surface of the second component. The grip facilitating means (36a, 36b) are configured in such a way that sliding first and second components along the longitudinal axis of the drug delivery device is substantially impossible. This can be achieved, for example, by providing ridges or troughs formed in the elastomeric material or added thereto, and optionally oriented, such that when compressed, said grip facilitating means exerts friction on the outer peripheral surface of the drug delivery device body, and thereby prevents any of said first and second component from sliding along said body, or even from rotating around said body.

As can be seen in FIG. 3, the first component (35b) also comprises a cutout section (39) to allow for placement of said component (35b) around a viewing window of the drug delivery device, as many devices currently on the market have a viewing window provided for the user, to display the selected dose in an analog or digital display window. The first component is also provided with projections 40, for example four generally upright projections (40) of the same material as the body of the first component. Each projection (40) is configured to present a substantially orthogonally projecting pair of shoulders (42) separated by a groove (41), which project outwards from the upright projections. The groove (41) enables the shoulders (42) of each pair of shoulders to be compressed slightly towards each other when downward pressure is brought to bear on them, for example, when the second component (35a), comprising a suitable corresponding slot (43, FIG. 6) is pressed down onto them. The functioning of the orthogonally projecting pairs of shoulders will be explained in relationship with the mounting sequence and assembly of the dose, control device hereinafter.

Figure 6:
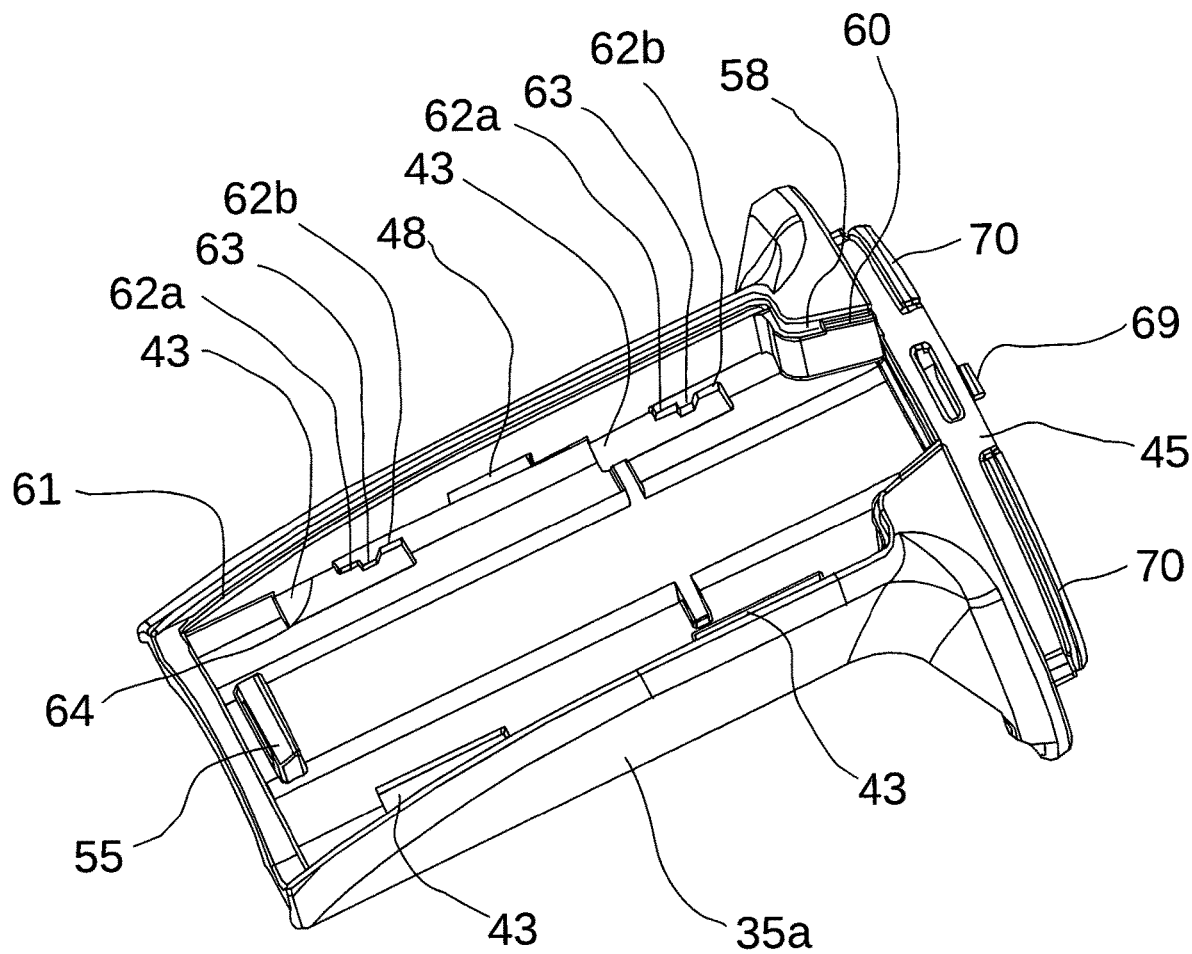
FIG. 6 is a schematic false perspective representation of an upper view of one of the components making up the dose control device and adapted to house the dose control system.

The second component (35a) as illustrated in more detail in FIGS. 5 and 6, is a housing that is configured to receive several other elements, and form a sub-unit that will mate with the first component and form an encasing unit defining a longitudinal bore about the outer peripheral surface of the body of the drug delivery device. As can be seen from FIG. 5, the second component (35a) has a substantially elongate part (44), corresponding to the remaining unencased area of the drug delivery device, and a substantially annular part (45), which is designed to surround the proximal extremity (22) of the drug delivery device. The substantially elongate part (44) is configured to be able to receive a dose control system, for example, mounted on a printed circuit board (46). The printed circuit board (46) comprises all of the electronic components of the dose control system as described above, e.g. central processing unit, real time clock, memory storage, magnetometers, accelerometer, communications subsystem, etc. As can be seen from the exploded view in FIG. 5, the printed circuit board (46) is also substantially elongate, and the substantially elongate part (44) of the second component is designed to position said dose control system in a substantial longitudinal alignment along the longitudinal axis (25) of the drug delivery device.

The printed circuit board further comprises downward facing projections (47) which also project out from the sides of said printed circuit board. These projections engage with corresponding slots (48) provided in the sides of the housing (35a) of said second component so as to seat said printed circuit board within said housing (35a). The printed circuit board, also comprises sprung loaded electrical pick ups or connectors (49) which are designed to allow contact between an anode or cathode of the power supply, in this case the batteries (32, 33), which are held in a circuit board cover (50). The circuit board cover has two battery housings (51, 52), one for each of the batteries (32, 33). The circuit board cover (50) is designed to completely encase the printed circuit board (46) and clips onto, and is maintained clipped thereto, with the help of downward facing projections (53) that have a substantially orthogonally inward facing shoulder. The inward facing shoulders of the projections (53) are designed to elastically push fit over the edge of the printed circuit board (46) and then catch on the underside face of said circuit board (46), thereby encasing said printed circuit board and preventing a user from tampering with it. Next, the printed circuit board (46) and circuit board cover (50) can be inserted into the housing 35a of the second component. As the printed circuit board is pushed down into the housing, it seats in the space provided for it within the housing and the seating projections (47) of the printed circuit board push fit against the inner walls of the housing (35a) until they meet the seating slots (48) of the housing (35a) at which point they fill said slots (48), and in so doing, the substantially orthogonally outward shoulders of said seating projections extend into said slots and outwards under an upper edge formed by contours of said slots, thereby preventing any upwards withdrawal of the printed circuit board and circuit board cover.

As can be further seen in FIG. 5, the housing 35a of the second component is also adapted and configured to enable insertion of a light window (54), allowing for passage of light from a light emitting means provided in the dose control means, for example, a LED, or other similar light emitting means. The housing (35a) further includes a locking hoop (55) or loop, for example, made of the same material as the body of the housing (35a), the function of which will be explained hereafter.

The batteries (32, 33) can now be placed in the battery holders (51, 52). At present, these batteries are not held in place, as they are pushed up by the spring loaded electrical connectors (49) of the circuit board (46) which exert a pushing force upwards from said printed circuit board through said battery holders onto the underside face of said batteries. A closure lid (56) or cover is also provided for the housing (35a). The closure lid (56) has a proximal extremity (57) that is shaped to match the contours of the corresponding proximal extremity (58) of the elongate part of the housing (35a), and is provided with a proximal ridge (59) that slides under, and engages with corresponding upper grooves (60) provided in the proximal extremity (58) of the housing (35a). The closure lid (56) is slidingly engaged along said grooves (61) provided in the upper part of the housing (35a) and is provided on its underside with a tongue (not shown) that engages the loop or hoop (55), preventing the lid (56) from being lifted up at its distal end. At the same time, the proximal ridge (59) is slid into and engages with the grooves (60) provided at the distal extremity (58) of the elongate part of the housing (35a). The spring loaded electrical contacts push up against the batteries in their holders and the batteries in turn push up against the closure lid (56), preventing it from sliding out of engagement with either the hoop (55) or the grooves (60). The second component is now a fully assembled subunit ready to be assembled with the first component (35b).

The first component (35b) is clipped onto the barrel, or body of the drug delivery device, via push fit. The first component is dimensioned to encase snugly the body of the drug delivery device, and one way of doing this is to make the first component out of an elastically deformable material that is dimensioned so that it has a diameter that is slightly smaller than the diameter defined by the outer peripheral surface of the drug delivery device body. In this way, when the housing (35b) is pushed onto the body at the proximal end of the device, the elastically deformable material first dilates to absorb the difference in diameter, and then closes in and encases said outer surface with a snap-fit or push-fit action. The grip facilitating means, when present, also help to stabilise housing (35b) against any unwanted or undesired translational or rotational movement. Next, the second housing (35a) is mounted on the body of the drug delivery device. This is achieved by slightly inclining the annular part (45) of the housing (35a) to slide it onto the outer peripheral surface of the body. As this occurs, the elongate part (44) of the housing (35a) is raised up and then brought down towards the first housing (35b). As the second housing (35a) is brought down towards the first housing (35b), the projections (40) of the first housing (35b) begin to engage in the seating slots (43) of said second housing (35a). Each seating slot (43) is provided with a respective recessed part (62a, 62b) and a projecting part (63), the overall diameter of the slot along the recessed and projecting part being less than the width of the orthogonally projecting pairs of shoulders (41). The recessed parts (62a, 62b) are designed to allow the orthogonal shoulders to elastically engage with said parts as the second component is brought down onto the first component, and the projecting part (63) has a width that substantially matches or slightly exceeds that of the groove (42) in each pair of shoulders. As the shoulders (41) move up and across the recessed parts (62a, 62b), the projecting part (63) pushes said shoulders apart, such that when the shoulders have passed the recessed parts and click fitted into the slot (43), they can not be withdrawn easily by upwards pulling. In fact withdrawal of the second housing (35a) can only occur if said housing is slid along the longitudinal axis in a proximal direction towards the proximal extremity, thereby allowing said shoulders to move in a translational movement along slot (43) into a wider dimensioned distal area (64), from where the second housing can then be lifted upwards and separated from the first housing (35b).

As seen in FIG. 5 in the exploded view, the device can further comprise a decorative or ornamental ring (65) that seats on and mates with the annular part (45) of the second housing (35b). This ring (65) is provided with shoulders (66) which define locating recesses (67) and annular grooves (68) enabling the ring (65) to be mounted onto the annular part (45) of the second housing (35a).

Figure 9:
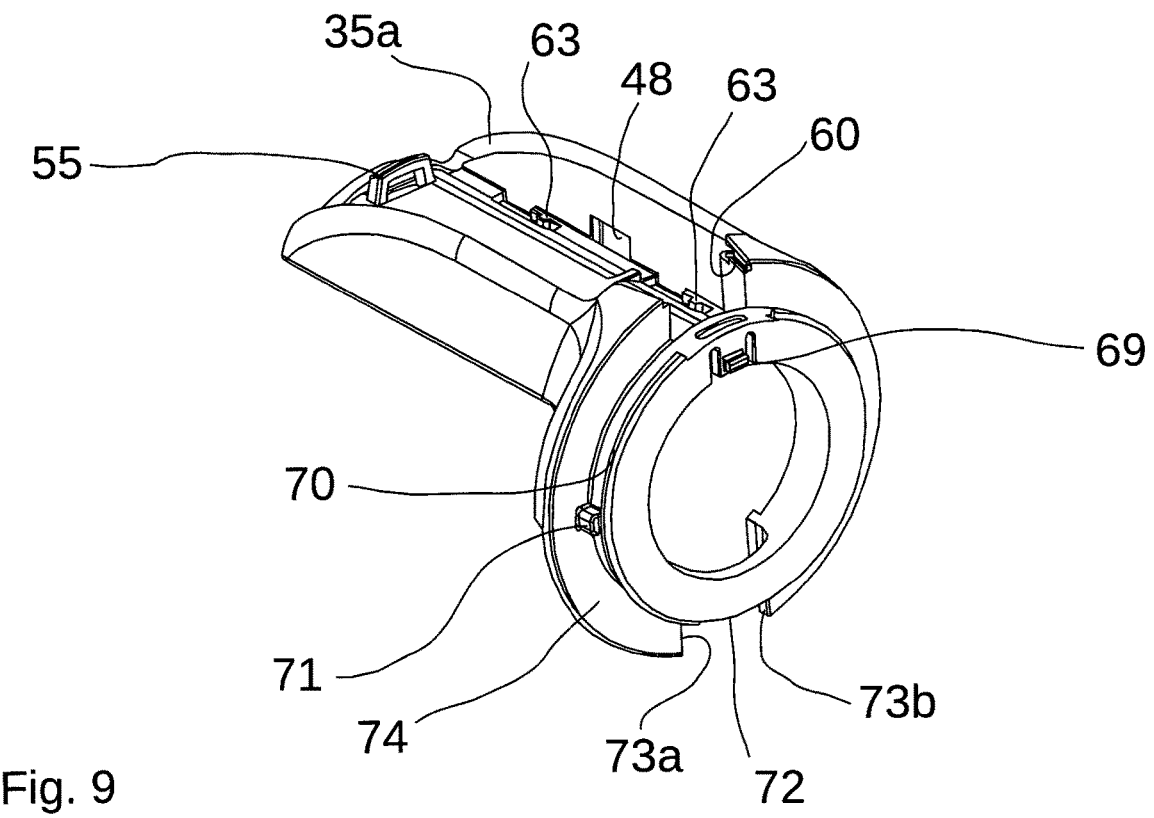
FIG. 9 is a false perspective representation of another upper view of one of the components making up the dose control device and adapted to house the dose control system.
Figure 10:
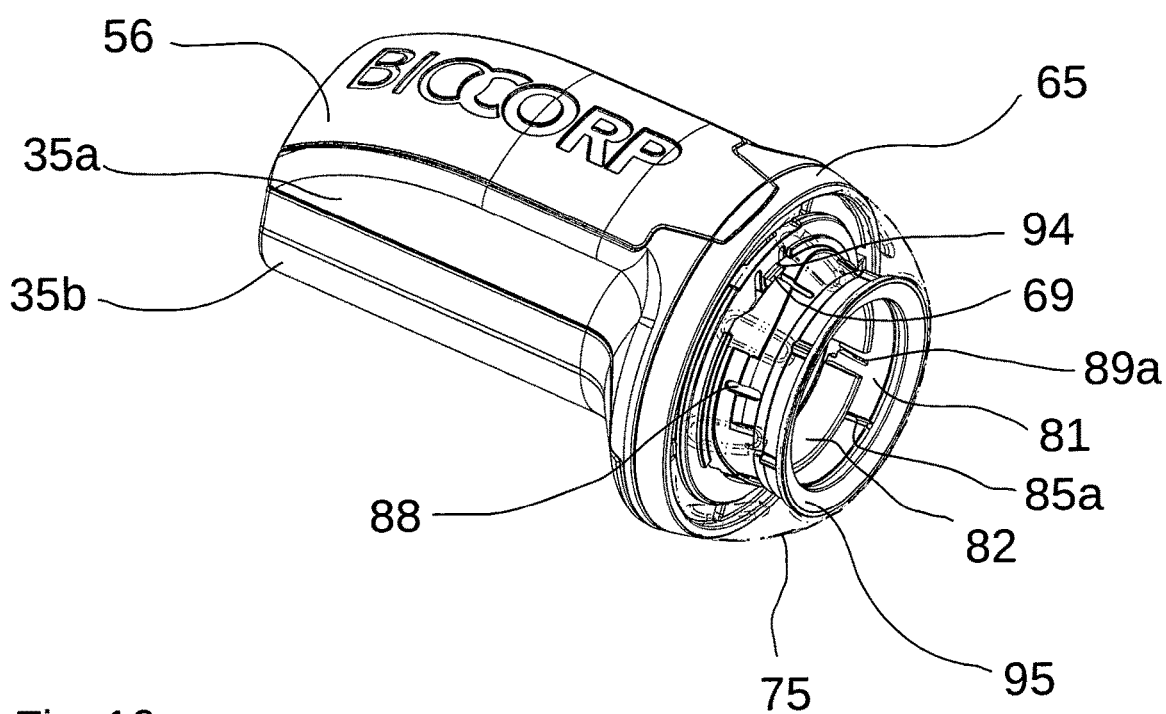
FIG. 10 is another false perspective view of the dose control device according to the present invention in an assembled, unmounted state, with some of the elements of the proximal end components made transparent for the purposes of understanding some more of the detail of the interaction of said components with each other.

The substantially annular part (45), illustrated in more detail in FIG. 6, is intended to surround the proximal extremity of the body of the drug delivery device as has been described above. This annular part (45) comprises further elements, including a projecting tongue (69) and annular ridges (70) which mate with the annular grooves of the ornamental ring (65). The tongue is designed to interact and function with the elements comprising the annular component (38) which will be further described hereafter. In FIG. 9, a different perspective view of the second housing (35a) is given, in which the annular part can be seen from a different angle. In this illustration, the tongue (69) is more clearly visible, projecting outwards from the rearwards, or proximal facing surface of the annular part (45). A positioning nub (71) is provided on the annular part (45) to facilitate positioning of the various elements of the annular component (38). In a lower part of the annular part, a gap (72), can be seen, defined by two spaced apart shoulders or ends (73a, 73b) of an annular flange 74. The gap (72) corresponds to the corresponding recess (39) in the first housing (35b) providing room to fit around a dose viewing window, as usually found on drug delivery devices in the art.

Turning back to FIG. 5 again, the annular component (38) comprises several elements, including the magnetic field producing means (MAG, 9). In this example, the magnetic field producing means is an annular plastomagnet (9), having two opposite magnetic poles, substantially arranged in diametric opposition around the ring shape. The annular magnet (9) is inserted into a selector wheel (75) in an annular groove (80) provided therein. The wheel (75) also has an annular flange surface (76) and an annular ridge (77) located around and outside of the groove (80). The annular flange surface ensures smooth contact with a corresponding annular flange surface on the ornamental ring, whereas the annular ridge is designed to move within an annular groove formed by the ornamental ring and the tightening ring (81). The wheel (75) also comprises inward projecting shoulders, or nubs (78), which are used to engage the wheel with the tightening ring, as will be explained hereafter.

Figure 7:
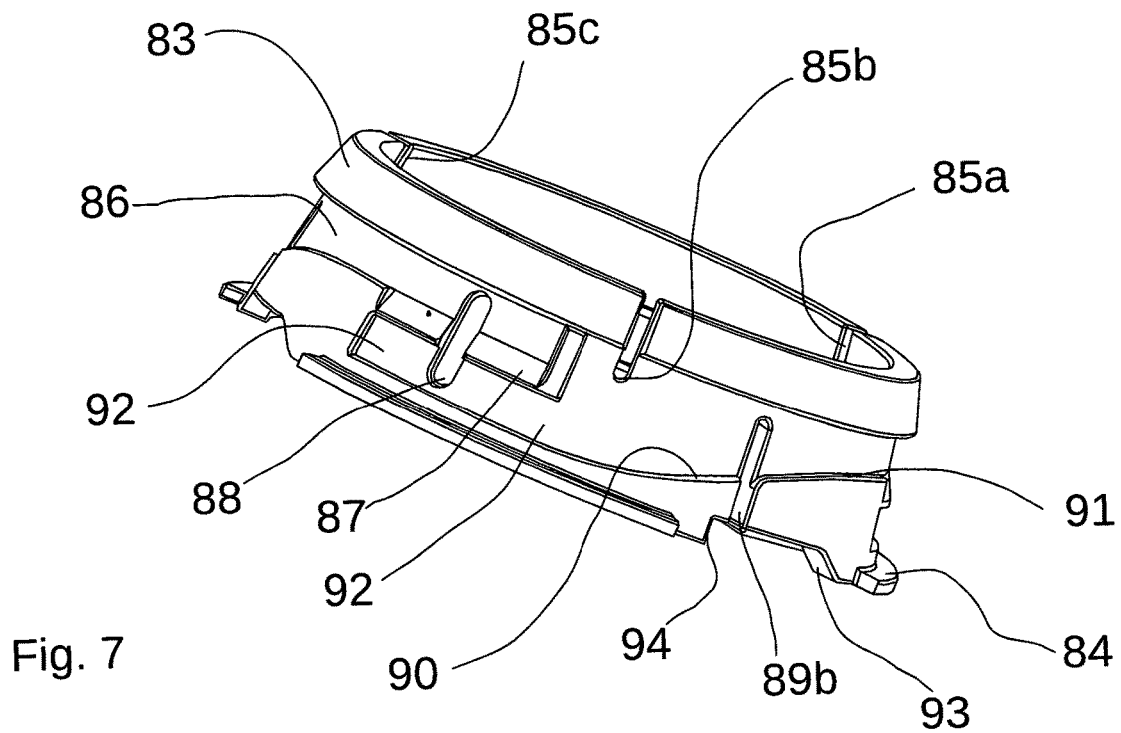
FIG. 7 is a schematic illustration of a first false perspective view of a tightening ring forming one of the components used to house the magnetic field producing means in the dose control device according to the present invention.
Figure 8:
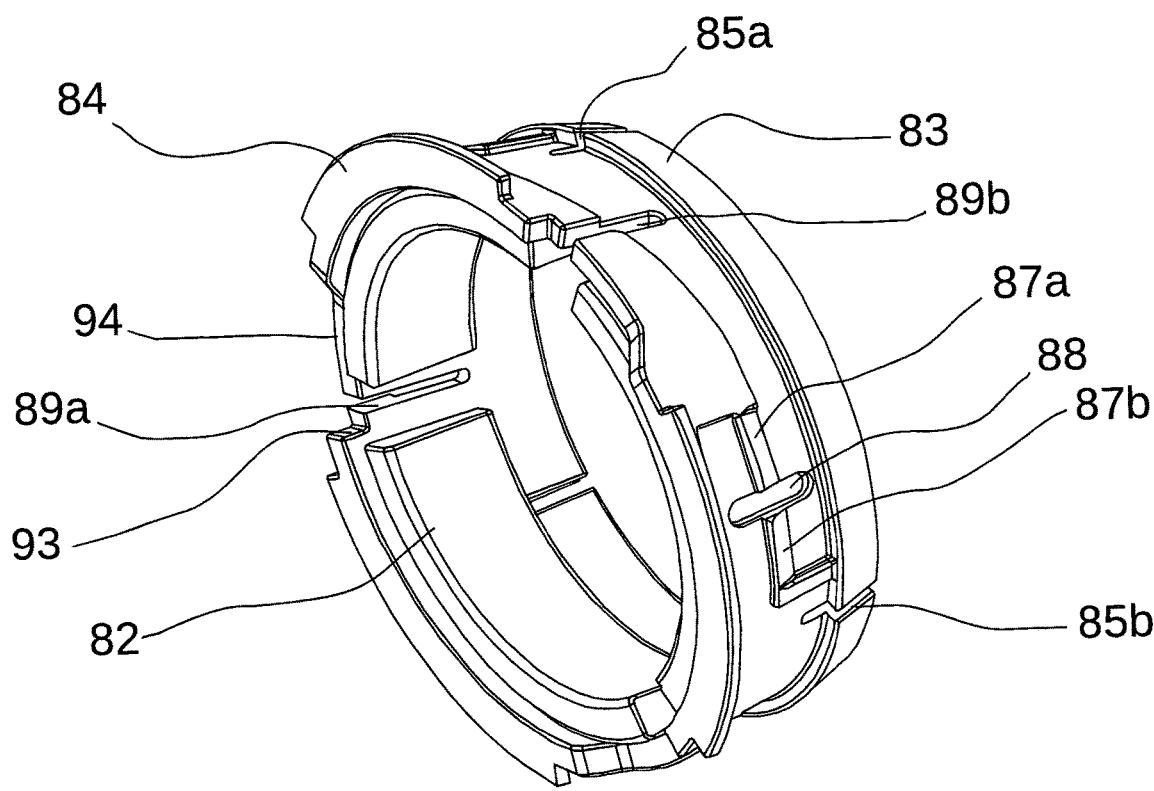
FIG. 8 is a schematic illustration of a another false perspective view of a tightening ring forming one of the components used to house the magnetic field producing means in the dose control device according to the present invention.

The tightening ring (81), as illustrated additionally in FIGS. 7 and 8, includes grip facilitating means (82), for example, elastomeric linings on an inner surface of said ring (81). These grip facilitating means (82) come into compressing contact with the outer surface of the dose selector wheel (28) and prevent the selector wheel (75) from slipping or sliding off the dose selector wheel (28).

The tightening ring (81) is inserted into the inner space defined by the bore of the wheel (75). As the tightening ring has a substantially conical or truncated cone shape, it has a smaller, proximal annular diameter and extends along the surface of a truncated cone towards a larger, distal annular diameter. At its proximal end, the tightening ring (81) therefore presents an outer conical surface (83) of substantially smaller radius than a corresponding distal flange. In between said proximal, smaller diameter conical annular surface and said distal flange (84), the tightening ring (81) is provided proximally with material cut-outs or compression slots (85a, 85b, 85c) located in the proximal, smaller diameter annular surface (83). These compression slots enable the tightening ring to be inserted in push-fit compression, undergoing elastic deformation as the ring is pushed inside the inner diameter of the selector wheel (75), which is constant, apart from the presence of the projecting nubs (78). As has been said above, the tightening ring (81) has a conical surface with an annular diameter that generally increases from the proximal end towards the distal end of the ring. However, the tightening ring also has a zone of reduced diameter (86) compared to the proximal annular surface (83), such that the latter annular surface (83) forms a ridge of greater diameter than the zone of reduced diameter (86), wherein the zone of reduced diameter is also of smaller diameter than that of the distal flange (84). The zone of reduced diameter (86) comprises several features designed to improve and facilitate assembly of the various elements comprising the annular component (38). As with the other parts of the ring, the zone of reduced diameter has a substantially truncated cone surface overall, expanding in diameter from the proximal end towards the distal end. In addition, the zone of reduced diameter comprises an area of more acute increase in truncated cone surface, or humps or ramps (87), arranged in pairs around an elliptical or rounded elongate slot (88). The slot (88) receives a projecting nodule (not shown) provided on the inner surface of the wheel (75) and said slot is located substantially perpendicularly to the ramps (87) which are disposed circumferentially around the zone of reduced diameter (86). The tightening ring (81) is inserted into the inner bore of the wheel (75). As insertion proceed, the projecting nubs (78) located on the inner surface of the wheel (75) bear down on the conical surface of the tightening ring (81), thereby causing elastic compression deformation of the ring, permitted thanks to the compression slots (85a, 85b, 85c) provided in said ring (81). As further insertion progresses, the nubs (78) bear down on the proximal conical surface, the diameter of which is increasing distally, until they overcome the initial resistance in the increasing diameter, and slip over the edge of said conical surface into the area of reduced diameter. Once in this position, the wheel (75) can not be removed from the tightening ring (81) without compromising the integrity of the system. The wheel (75) is thus initially seated on the tightening ring, or vice versa.

In the zone of reduced diameter (86), the tightening ring (81) also comprises a circumferential ridge (90), that is defined by a spline curve, starting at a proximal area (91) of the zone of reduced diameter, the ridge (90) extending down across and through said zone of reduced diameter to an area (92) distal of the ramps (87). This spline curve ridge (90) therefore starts in area (91) where the diameter of the cone is relatively smaller than at the end (92) of the ridge, where the conical surface has a relatively greater diameter, as it lays distally, and near to the distal flange (84).

As the tightening ring (81) and wheel (75) are now inserted onto, and brought to bear on, the outer surface of the dose selector wheel (28), the inner surface of the tightening ring is pushed radially outwardly, compressing the elastomer lining. This outwards radial expansion of the tightening ring is facilitated by expansion slots (89a, 89b) provided in the distal part of the tightening ring (81). The projecting nubs (78) now start to move downwards to the distal extremity of the tightening ring (81) and encounter the ramps (87) causing more elastic expansion of the tightening ring (81) and wedging the annular magnet into place within the annular groove (80).

From the position in which the tightening ring's inner surface (81) bears down on the ramps (87), the dose selector wheel (28) is gripped firmly by the inner wall of the tightening ring (81), and the annular component (38) is successfully mounted on said dose selector wheel. The wheel (75) can thus rotate about the longitudinal axis of the device, in direct correspondence to, and enabling direct rotation of the dose selector wheel (28), due to the latter being held by the inner surface of the tightening ring (81).

Further, optional, counter-clockwise rotation of the tightening ring (81) when viewed from the proximal end of the annular component causes the projection nubs (78) to bear down on the ramps (87) and then finally overcome them to one side thereof, leaving the nubs (78) in the distal area (92) of the tightening ring (81).

If the dose control device needs to be reset, or repositioned, for example, due to user manipulation error, causing the reference point for drug dosage selection and administration to be no longer valid, then the tightening ring (81) makes use of a recessed land (93) and abutment shoulder provided in the distal flange area of the tightening ring (81). This can happen for example in the case of a drug delivery device that doesn't depend on the wheel (75) being rotated back to the reference point, but rather translates the wheel (75), dose selector wheel (28) and dose selector shaft distally along the longitudinal axis (25) back to a distal position in abutment or near abutment with the proximal extremity of the body of the drug delivery device. In such a situation, the wheel (75) can be rotated about the longitudinal axis (25), past its normal limit of movement, causing the projection nubs (78) to move into abutment against and follow the path of the spline curve ridge (90). When the projection nubs reach the orthogonally located elongated rounded slot, the nodule engages therein, causing the rotation movement of the wheel to stop. However, this then causes the movement vector to be applied to the distal flange, which rotates, and then the recessed land (93) moves over the tongue (69), which can deform elastically, until the abutment shoulder (94) is reached at which point the tongue (69) is in abutment with said shoulder (94). At this point, the device is once again at the reference point for selecting and administering drug doses.

Finally, the annular component (28) is also provided with a closure ring (95), which is inserted proximally into the proximal opening of the wheel (75) and is provided with mating projections (96) to facilitate elastic push-fit compression and location of an annular mating surface (97) within a groove provided proximally in the wheel (75).

The invention claimed is:

1. A dose control device adapted to be removably mounted onto an exterior peripheral surface of a drug delivery device including:
   a body extending along a longitudinal axis and having a distal and proximal extremity,
   a dose selector wheel rotatably mounted outside the body at the proximal extremity of the body and being configured for longitudinal displacement of a dose selector shaft along the longitudinal axis in response to rotation of said dose selector wheel with respect to the body,
   wherein the dose control device comprises:
   a first component configured to fit and encase a first portion of a circumference of an exterior peripheral surface of the body, and located at the proximal extremity of said body;
   a second component configured to fit and encase a second portion of the circumference of the exterior peripheral surface of said body, and also located at the proximal extremity of said body; said first component and said second component removably engage with each other to form a unit having a longitudinal bore that extends along the longitudinal axis of said body such that the entire circumference of the exterior peripheral surface at the proximal extremity of the body is encased between said first component and said second component, said first component and said second component are configured to snugly fit the exterior peripheral surface of said body to preclude displacement of any portion of said first and second components relative to the body;
   an annular component mounted on the dose selector wheel along the longitudinal axis and being configured to impart a rotational movement about said longitudinal axis to the dose selector wheel and to the dose selector shaft, and having means for producing a three-dimensional magnetic field;
   magnetic field detection means mounted in one of said first and second components and being configured to detect changes in the magnetic field produced by the means for producing a three-dimensional magnetic field;
   an integrated processing unit connected to the magnetic field detection means, and being configured for calculating a position of the means for producing a three-dimensional magnetic field with respect to the magnetic field detection means in accordance with said changes in the magnetic field.

2. The dose control device according to claim 1, wherein the means for producing a three-dimensional magnetic field is an annular magnet with a first magnetic pole and a second magnetic pole of opposite polarity to the first magnetic pole, the two poles being diametrically opposed within the annular magnet.

3. The dose control device according to claim 2, wherein each of the two diametrically opposed poles is located in a respective half of the annular component.

4. The dose control device according to claim 1, wherein the three-dimensional magnetic field producing means is selected from the group consisting of ferrite, sintered ferrite, composite materials made up of a thermoplastic matrix and isotropic neodymium-iron-boron powder, composite materials made up of a thermoplastic matrix and strontium-based hard ferrite powder, composite materials made of a thermohardening matrix and isotropic neodymium-iron-boron powder, magnetic elastomers produced with heavily charged strontium ferrite powders mixed with synthetic rubber or PVC, flexible calendered composites formed from a synthetic elastomer charged with strontium ferrite grains, laminated composites of flexible calendered composites co-laminated with a soft iron-pole plate, neodymium-iron-boron magnets, magnetized steels made of aluminium-nickel-cobalt alloy, and alloys of samarium and cobalt.

5. The dose control device according to claim 1, further comprising grip facilitating means for facilitating grip of the first component and/or the second component on the exterior peripheral surface of the drug delivery device.

6. The dose control device according to claim 1, further comprising an elastomeric lining located on an inner surface of said first, and/or said second component, to increase grip of said first and/or said second component on the exterior peripheral surface of the drug delivery device.

7. The dose control device according to claim 1, wherein said first component and/or said second component, either individually, or in cooperation, comprise an annular portion or semi-annular portion, which engages with the outer peripheral surface of the body at the proximal extremity.

8. The dose control device according to claim 1, wherein said first component or said second component comprises a display window for display of a selected dose of a drug disposed inside the drug delivery device.

9. The dose control device according to claim 1, wherein the annular component further comprises grip facilitating means for facilitating grip of an inner surface of the annular component on an exterior surface of the dose selector shaft.

10. The dose control device according to claim 1, wherein the magnetic field detection means include at least one magnetometer.

11. The dose control device according to claim 1, wherein the magnetic field detection means include at least two magnetometers.

12. The dose control device according to claim 1, further comprising displacement detection means configured to measure a relative displacement or relative movement of the drug delivery device in a predetermined direction.

13. The dose control device according to claim 12, wherein the integrated processing unit is connected to the displacement detection means, for processing information received from both the magnetic field detection means and the displacement detection means.

14. The dose control device according to claim 13, wherein the integrated processing unit is mounted on a printed circuit board located within said first component or said second component.

15. The dose control device according to claim 13, further comprising communication means configured to enable communication of information from the integrated processing unit with a remote and/or local data processing system.

16. The dose control device according to claim 15, further comprising a unique identifier that is communicated to the remote and/or local data processing system.

17. The dose control device according to claim 15, further comprising time determination means.

18. The dose control device according to claim 15, further comprising autonomous power supply means.

19. The dose control device according to claim 12, wherein the displacement detection means comprise at least one accelerometer configured to detect:
 a relative movement of acceleration caused by a vibration of the dose selector shaft; and/or
 a priming movement of acceleration of the dose selector shaft along the longitudinal axis of the drug delivery device; and/or
 an injection positioning of the drug delivery device indicating that said drug delivery device is in a position ready for an injection operation to occur; and/or
 a purge position of the drug delivery device indicating that said drug delivery device is in a position ready for a purge operation to occur; and/or
 a position of the drug delivery device anywhere between an injection position and a purge position.

20. The dose control device according to claim 1, further comprising at least one accelerometer.

21. The dose control device according to claim 1, further comprising temperature detection means.

22. The dose control device according to claim 1, wherein the three-dimensional magnetic field producing means is configured to effect a rotating coaxial displacement around, and along, the longitudinal axis, and wherein the integrated processing unit is configured for calculating rotating coaxial displacement of said annular component with respect to one of said first and second components.

23. The dose control device according to claim 1, wherein the magnetic field detection means is further configured to detect the earth's magnetic field (EMF).

24. The dose control device according to claim 1, wherein the magnetic field detection means comprises at least first and second magnetometers, wherein the first magnetometer and the second magnetometer are configured to operate in parallel, both magnetometers simultaneously detecting any changes in a magnetic field, as the three-dimensional magnetic field producing means is displaced away from or towards the first magnetometer and the second magnetometer.

25. The dose control device according to claim 1, wherein the magnetic field detections means comprises at least first and second magnetometers, wherein the first magnetometer and the second magnetometer are configured to operate in series, whereby the first magnetometer detects changes in a magnetic field until a predetermined value of the magnetic field is detected, and in response to detection of said predetermined value the dose control device is configured to activate the second magnetometer to detect changes in the magnetic field beyond said predetermined value, as the three-dimensional magnetic field producing means is displaced away from or towards the first and second magnetometers.

26. The dose control device according to claim 1, wherein said dose control device is configured to permit an unhindered or unchanged modus operandi of said drug delivery device compared to an injectable drug delivery device without said dose control device.

* * * * *